US012575726B2

(12) United States Patent
Bagherinia et al.

(10) Patent No.: US 12,575,726 B2
(45) Date of Patent: Mar. 17, 2026

(54) METHOD AND SYSTEM FOR CHOROID-SCLERAL SEGMENTATION USING DEEP LEARNING WITH A CHOROID-SCLERAL LAYER MODEL

(71) Applicant: Carl Zeiss Meditec, Inc., Dublin, CA (US)

(72) Inventors: Homayoun Bagherinia, Oakland, CA (US); Lars Omlor, Pleasanton, CA (US)

(73) Assignee: CARL ZEISS MEDITEC, INC., Dublin, CA (US)

( * ) Notice: Subject to any disclaimer, the term of this patent is extended or adjusted under 35 U.S.C. 154(b) by 618 days.

(21) Appl. No.: 18/085,062

(22) Filed: Dec. 20, 2022

(65) Prior Publication Data

US 2023/0190095 A1 Jun. 22, 2023

Related U.S. Application Data

(60) Provisional application No. 63/291,602, filed on Dec. 20, 2021.

(51) Int. Cl.
*A61B 3/10* (2006.01)
*G06T 7/00* (2017.01)

(52) U.S. Cl.
CPC ............ *A61B 3/102* (2013.01); *G06T 7/0012* (2013.01); *G06T 2207/20081* (2013.01)

(58) Field of Classification Search
CPC .......... A61B 3/102; G06T 7/0012; G06T 7/11
USPC ........................................................ 351/200
See application file for complete search history.

(56) References Cited

U.S. PATENT DOCUMENTS

| | | | |
|---|---|---|---|
| 6,549,801 B1 | 4/2003 | Chen et al. | |
| 7,301,644 B2 | 11/2007 | Knighton et al. | |
| 9,332,902 B2 | 5/2016 | Tumlinson et al. | |
| 9,456,746 B2 | 10/2016 | Bublitz et al. | |
| 2005/0171438 A1 | 8/2005 | Chen et al. | |
| 2010/0027857 A1 | 2/2010 | Wang | |
| 2012/0277579 A1 | 11/2012 | Sharma et al. | |
| 2012/0307014 A1 | 12/2012 | Wang | |

(Continued)

FOREIGN PATENT DOCUMENTS

| | | | |
|---|---|---|---|
| WO | 2016124644 | 5/2012 | |
| WO | 2012059236 | 8/2016 | |
| WO | WO-2020165196 A1 * | 8/2020 | .............. G06T 7/37 |

OTHER PUBLICATIONS

Kugelman, J. et al. "Automatic choroidal segmentation in OCT images using supervised deep learning methods," Scientific Reports vol. 9, Article No. 13298. (2019) 9:13298 | https://doi.org/10.1038/s41598-019-49816-4 (Year: 2019).*

(Continued)

*Primary Examiner* — Brandi N Thomas
*Assistant Examiner* — Boutsikaris Leonidas
(74) *Attorney, Agent, or Firm* — SNELL & WILMER L.L.P.

(57) ABSTRACT

A System/Method/Device for segmenting the choroid-scleral layer from an optical coherent tomography (OCT) volume scan. The present system uses a deep learning machine model based on a neural network that include multiple convolution layers, but no deconvolution layers. Rather, the present neural network is based on a novel architecture based on the discrete cosine transform.

20 Claims, 16 Drawing Sheets

70

71
Collecting OCT Image Data (Volume Scan) of an Eye

73
Submit the OCT Image Data to a Deep Learning Machine Model (based on a Neural Network) to Produce an Initial Choroid-sceral Layer Segmentation. The Neural Network having an Encoding Including Convolution Layers Followed by a Decoding Path based on Discrete Cosine Transforms 75
Submit the Initial Choroid-scleral Layer Segmentation to Uncertainty Detection (an Authentication or Classification Module) that Tests the General Shape of the Initial Choroid-scleral Layer Segmentation, and Excludes any Regions Deemed to have a Shape Inconsistent with that of Know/expected Choroid-seleral 77
Fill-in the Missing Regions, such as by Interpolation, to Define a Final Choroid-scleral Layer Segmentation

(56) References Cited

U.S. PATENT DOCUMENTS

| | | | |
|---|---|---|---|
| 2015/0131050 A1 | 5/2015 | Bublitz et al. | |
| 2019/0272631 A1* | 9/2019 | Shemonski | A61B 3/102 |

OTHER PUBLICATIONS

Bagherinia, H. et al. "A method for automated choroidal-scleral interface segmentation in optical coherence tomography," ARVO Journals, IOVS 2019, vol. 60, Issue 9. iovs.arvojournals.org/article. aspx?articleid=2745.

Hu, Z. et al. "Semiautomated Segmentation of the Choroid in Spectral-Domain Optical Coherence Tomography Volume Scans," ARVO Journals IOVS 2013, vol. 54, Issue 3. iovs.arvojournals.org/article.aspx?articleid=2165971.

Oakley, J. et al. "Automated choroid segmentation of SD-OCT volumes using deep learning," IOVS 2019, vol. 60, Issue 1, ARVO Imaging in the Eye Conference Abstract. Investigative Ophthalmology & Visual Science.

Zhang. H. et al. "Automatic Segmentation and Visualization of Choroid in OCT with Knowledge Infused Deep Learning," IEEE Journal of Biomedical and Health Informatics 2020.

Sui, X. et al. "Choroid segmentation from Optical Coherence Tomography with graph-edge weights learned from deep convolutional neural networks," Neurocomputing, vol. 237, May 10, 2017, pp. 332-341. www.elsevier.com/locate/neucom.

Srivastava, R. et al. "Choroid Segmentation in Optical Coherence Tomography Images Using Deep Learning," ICBME 2019: 17th International Conference on Biomedical Engineering pp. 31-40. www.researchgate.net/publication/34839725 DOI: 10.1007/978-3-030-62045-5_4.

Kugelman, J. et al. "Automatic choroidal segmentation in OCT images using supervised deep learning methods," Scientific Reports vol. 9, Article No. 13298. (2019) 9:13298 | https://doi.org/10.1038/s41598-019-49816-4.

Tsuji, S. et al., "Semantic Segmentation of the Choroid in Swept Source Optical Coherence Tomography Images for Volumetrics," Scientific Reports vol. 10, Article No. 1088 (2020) 10:1088 | https://doi.org/10.1038/s41598-0202-57788-z.

He, F. et al. "Choroid Segmentation of Retinal OCT Images Based on CNN Classifier and I2-Iq Fitter," Computational and Mathematical Methods in Medicine, 2021. vol. 2021 Art ID. 8882801. https://doi.org/10.1155/2021/8882801.

Zhou, H. et al. "Attenuation correction assisted automatic segmentation for assessing choroidal thickness and vasculature with swept-source OCT," Biomedical Optics Express vol. 9, No. 12, pp. 6067-6080 (2018). https://doi.org/10.1364/BOE.9.006067.

Hillmann, D. et al., "Holoscopy—holographic optical coherence tomography" Optics Letters vol. 36, No. 13. p. 2390. 2011 Optical Society of America.

Nakamura, Y. et al., "High-Speed three dimensional human retinal imaging by line field spectral domain optical coherence tomography" Optics Express vol. 15, No. 12 p. 7103. 2007 Optical Society of America.

Blazkiewicz et al., "Signal-to-noise ratio study of full-field Fourier-domain optical coherence tomography," Applied Optics. vol. 44, No. 36. p. 7722. 2005 Optical Society of America.

* cited by examiner

| | Input Layer | | Dropout |
|---|---|---|---|
| | Convolution (2D) + Activation | | Discrete Cosine Transform (DCT) |
| | Max Pooling (2D) | | Max Pooling |

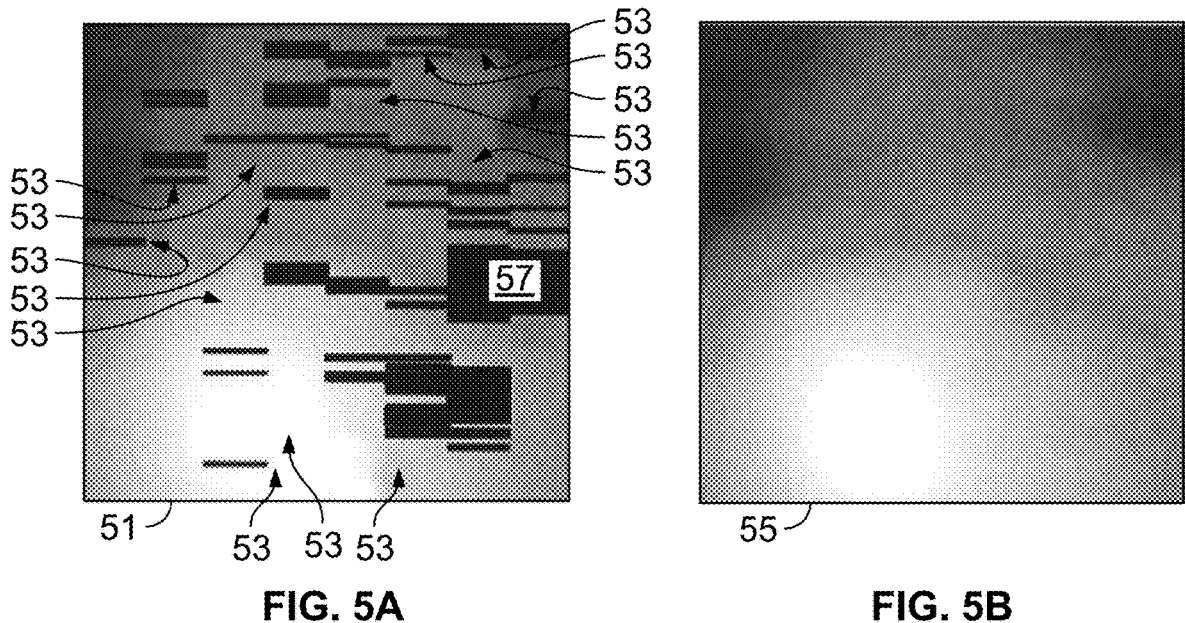
FIG. 5A
FIG. 5B
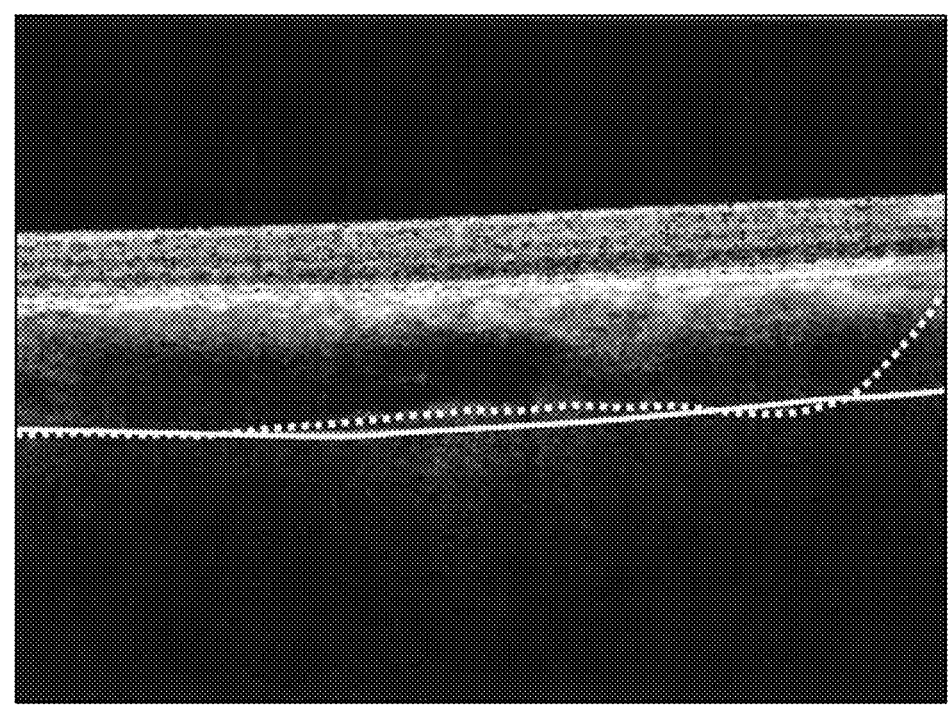
FIG. 6A

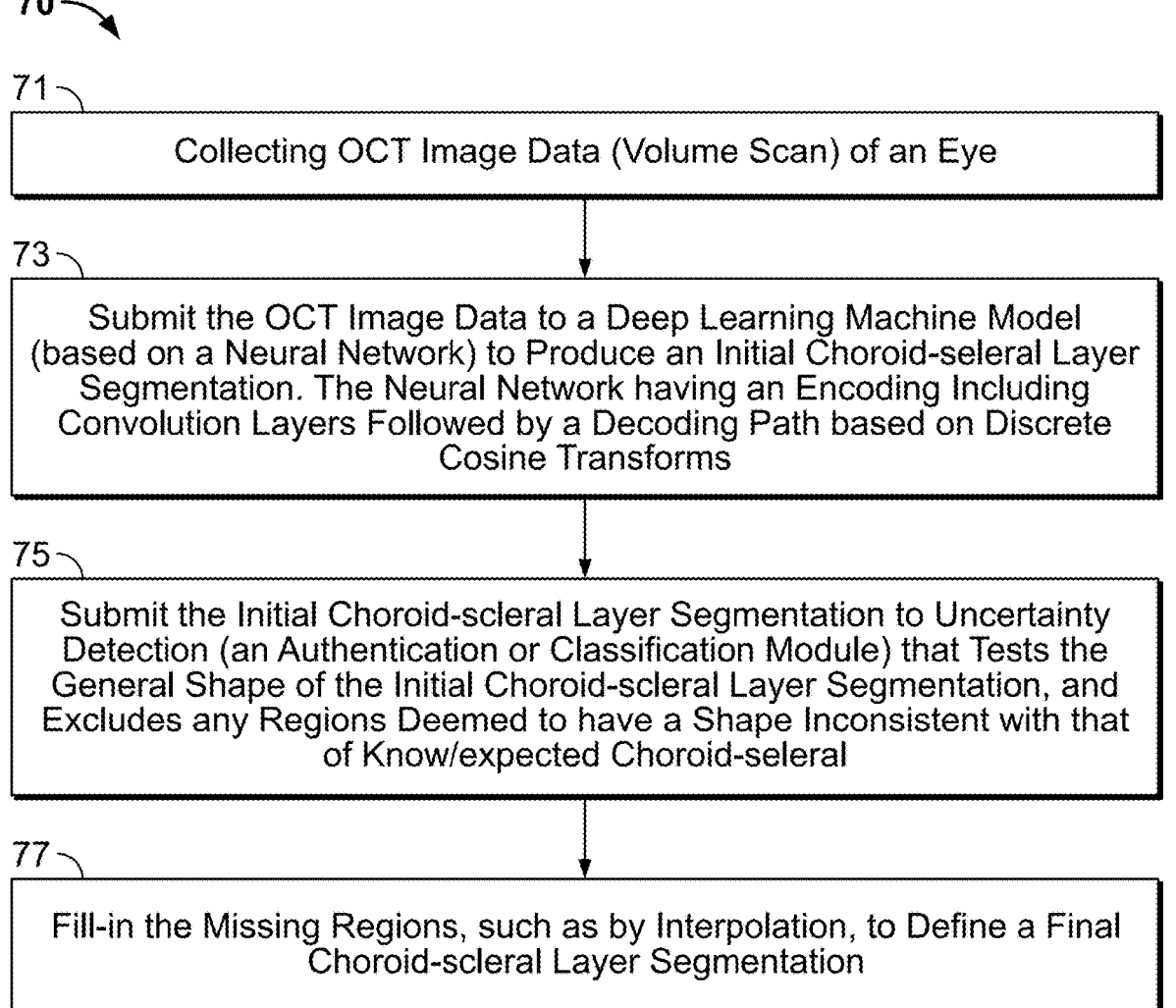

70

71

Collecting OCT Image Data (Volume Scan) of an Eye

73

Submit the OCT Image Data to a Deep Learning Machine Model (based on a Neural Network) to Produce an Initial Choroid-seleral Layer Segmentation. The Neural Network having an Encoding Including Convolution Layers Followed by a Decoding Path based on Discrete Cosine Transforms

75

Submit the Initial Choroid-scleral Layer Segmentation to Uncertainty Detection (an Authentication or Classification Module) that Tests the General Shape of the Initial Choroid-scleral Layer Segmentation, and Excludes any Regions Deemed to have a Shape Inconsistent with that of Know/expected Choroid-seleral

77

Fill-in the Missing Regions, such as by Interpolation, to Define a Final Choroid-scleral Layer Segmentation

FIG. 7

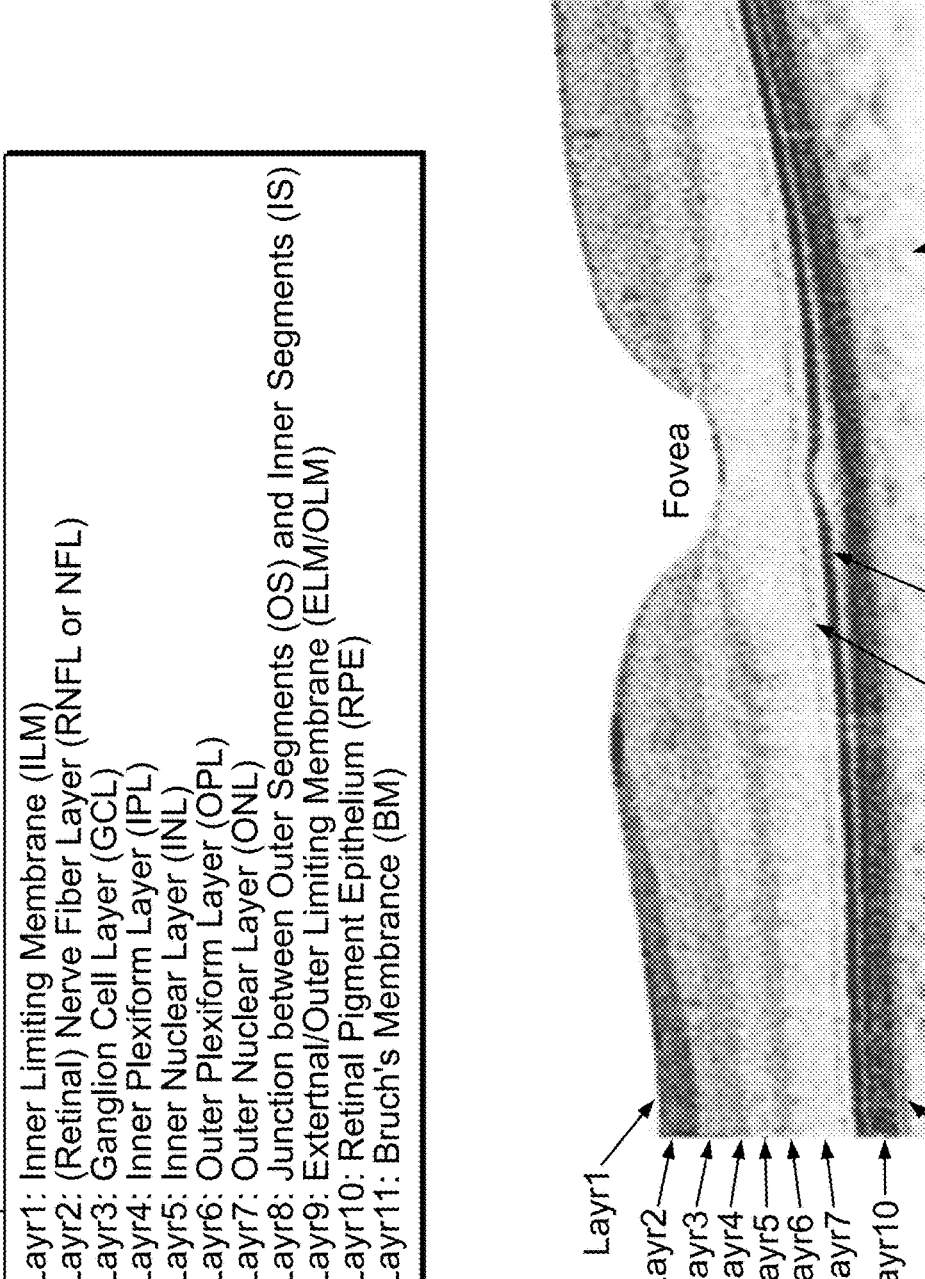

910

Layr1: Inner Limiting Membrane (ILM)
Layr2: (Retinal) Nerve Fiber Layer (RNFL or NFL)
Layr3: Ganglion Cell Layer (GCL)
Layr4: Inner Plexiform Layer (IPL)
Layr5: Inner Nuclear Layer (INL)
Layr6: Outer Plexiform Layer (OPL)
Layr7: Outer Nuclear Layer (ONL)
Layr8: Junction between Outer Segments (OS) and Inner Segments (IS)
Layr9: Extertnal/Outer Limiting Membrane (ELM/OLM)
Layr10: Retinal Pigment Epithelium (RPE)
Layr11: Bruch's Membrane (BM)

METHOD AND SYSTEM FOR CHOROID-SCLERAL SEGMENTATION USING DEEP LEARNING WITH A CHOROID-SCLERAL LAYER MODEL

CROSS-REFERENCE TO RELATED APPLICATIONS

This application claims the benefit of priority under 35 U.S.C. 120 to U.S. Provisional Application Ser. No. 63/291, 602 entitled "CHOROID-SCLERAL SEGMENTATION USING DEEP LEARNING AND CHOROID-SCLERAL LAYER MODEL", filed on Dec. 20, 2021, the entire contents of which are incorporated by reference for all purposes.

FIELD OF INVENTION

The present invention is generally directed to retinal layer segmentation in optical coherence tomography (OCT) data. More specifically, it is directed to an optimized deep-learning architecture for retinal layer segmentation.

BACKGROUND

OCT is a non-invasive imaging technique that uses light waves to penetrate tissue and produce image information at different depths within the tissue, such as an eye. Generally, an OCT system is an interferometric imaging system based on detecting the interference of a reference beam and backscattered light from a sample illuminated by an OCT beam. Each scattering profile in the depth direction (e.g., z-axis or axial direction) may be reconstructed individually into an axial scan, or A-scan. Cross-sectional slice images (e.g., two-dimensional (2D) bifurcating scans, or B-scans) and volume images (e.g., 3D cube scans, or C-scans) may be built up from multiple A-scans acquired as the OCT beam is scanned/moved through a set of transverse (e.g., x-axis and/or y-axis) locations on the sample. When applied to the retina of an eye, OCT generally provides structural data that, for example, permits one to view distinctive tissue layers and vascular structures of the retina. OCT angiography (OCTA) expands the functionality of an OCT system to also identify (e.g., render in image format) the presence, or lack, of blood flow in retinal tissue. For example, OCTA may identify blood flow by identifying differences over time (e.g., contrast differences) in multiple OCT scans of the same retinal region, and designating differences in the scans that meet predefined criteria as blood flow.

An attraction of using machine learning approaches, particularly artificial intelligence (AI) approaches, is that they may make use of concepts overlooked by more traditional knowledge-based approaches, and their operation can sometimes be faster than more traditional approaches. Although there are many AI architectures, each typically optimized to work with specific types of data, such as text or images, a general difficulty associated with most AI approaches is the training process. A large library of training and testing examples is not only needed, but the actual training process can be computer-resource intensive and require a long time to execute. This can make revising and retraining difficult.

It is an object of the present invention to reduce some of the difficulties associated with training an AI architecture typically associated with images.

It is another object of the present invention to provide a new convolutional neural network (CNN) that achieves a similar result as traditional CNNs with fewer training stages and model parameters.

SUMMARY OF INVENTION

The above objects are met in a method/system for segmenting a choroid-scleral layer from optical coherence tomography (OCT) image data (e.g., volume scan or C-scan) of an eye. The method/system includes collecting (or acquiring) the OCT image data of the eye from/with an OCT system, and submitting the OCT image data to a deep learning machine model based on a neural network, which produces an initial choroid-scleral layer segmentation. The neural network preferably has a contracting (or encoding) path having multiple convolution layers followed by a max pooling layer; and an expanding (decoding) path following the contracting path, where the expanding path includes at least one discrete cosine transform (DCT) decoder. Preferably the neural network includes an inverse DCT followed by the DCT mentioned above. Also, the expanding path may lack any deconvolution module. The initial choroid-scleral layer segmentation is submitted to uncertainty detection (e.g., an authentication test or classification module) to identify and exclude, from the initial choroid-scleral layer segmentation, patch regions deemed to have incorrect segmentation and define a final choroid-scleral layer segmentation. The final choroid-scleral layer segmentation is preferably defined by filling in the excluded/removed patch regions, such as by interpolation, extrapolation, polynomial fitting, Zernike fitting, Gridfit, etc.

Optionally, multiple adjacent B-scans from the volume scan are input for simultaneous/parallel choroid-scleral segmentation, such as to define a 3D initial choroid-scleral layer segmentation with high correlation at the choroid region. That is, the deep learning model enforces continuity of the segmented initial choroid-scleral layer between the plurality of adjacent B-scans.

Any of multiple types of OCT systems, such as those discussed below may be used to acquire the OCT image data (volume scan). For example, the OCT system may include a light source for generating a beam of light, a beam splitter having a beam-splitting surface for directing a first portion of the light into a reference arm and a second portion of the light into a sample arm, optics for directing the light in the sample arm to one or more locations on a sample, a detector for receiving light returning from the sample and reference arms and generating signals in response thereto; and a processor for converting the signals into said OCT image data.

In embodiments, the deep learning machine model is based on a neural network trained using a set of training input images and a set of training output images, where each training output image is based on a corresponding training input image that has undergone attenuation correction, including removing of vessel shadows and improving contrast.

Optionally, the contracting path may include a relu-nonlinearity with 3×3 filter size followed by the max pooling layer. As mentioned above, the contracting path defines an encoder, and the max pooling layer may determine a bottleneck size of the encoder that best reflects the energy distribution of the discrete cosine transform decoder. In this case, the expanding path defines a decoder, and the first step in the decoding operation of the decoder is an inverse cosine transform with the bottleneck size and followed by a plurality of convolutional layers. Additionally, the penultimate layer of the decoder includes zero-padding from the bottleneck size to the size of the originally submitted OCT image data combined with the discrete cosine transform to provide an image up-sampling function.

In embodiments, at least one discrete cosine transform (DCT) decoder computes the discrete cosine transform along the width and height dimensions. Additionally, the OCT image data of an eye is a volume scan that is divided into 3D patches, and the OCT image data that is submitted to the deep learning machine model is a 3D patch.

The classification module (process) may use choroid-scleral interface attributes, including an attribute of smooth surface with low frequency component, to identify incorrect segmentation patch regions of the initial choroid-scleral layer. Alternatively, the classification module identifies patch regions of incorrect segmentation based on a linear fit between the choroid-scleral interface and a smooth surface. Also, the classification module may identify patch regions of incorrect segmentation based on one or more of outlier patches from a max curvature or arclength, unrealistic shapes defined as deviating beyond a predefined amount from a library of acceptable shapes, and choroid-scleral interface modeling based on polynomial, Zernike, or Gridfit.

Other objects and attainments together with a fuller understanding of the invention will become apparent and appreciated by referring to the following description and claims taken in conjunction with the accompanying drawings.

Several publications may be cited or referred to herein to facilitate the understanding of the present invention. All publications cited or referred to herein, are hereby incorporated herein in their entirety by reference.

The embodiments disclosed herein are only examples, and the scope of this disclosure is not limited to them. Any embodiment feature mentioned in one claim category, e.g., system, can be claimed in another claim category, e.g., method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

In the drawings wherein like reference symbols/characters refer to like parts:

FIG. 5A shows an image of a 2D choroid-scleral map with removed (inferior or unacceptable) regions of uncertainty displayed as dark rectangles on the image in accordance with various embodiments.

FIG. 5B shows an image in which the removed regions of uncertainty are in the image of FIG. 5A has been filled in using imaging techniques such as interpolates/extrapolates to produce a corrected 2D choroid-scleral map in accordance with various embodiments.

FIGS. 6A, 6B, 6C, 6D, 6E, and 6F show examples of a set of OCT B-scans with choroid-scleral interface computed by multi-retinal layer segmentation (MLS) algorithm that measures intra-retinal layers boundaries comprising a dashed line and a solid line in accordance with various embodiments.

FIG. 7 illustrates an exemplary flowchart of a workflow of the choroid-scleral layer segmentation process in accordance with various embodiments.

FIG. 10 illustrates a diagram of an exemplary OCT B-scan image of a normal retina of a human eye with multiple identified canonical retinal layers and boundaries in accordance with various embodiments.

DESCRIPTION OF THE PREFERRED EMBODIMENTS

Figures 1, 2:
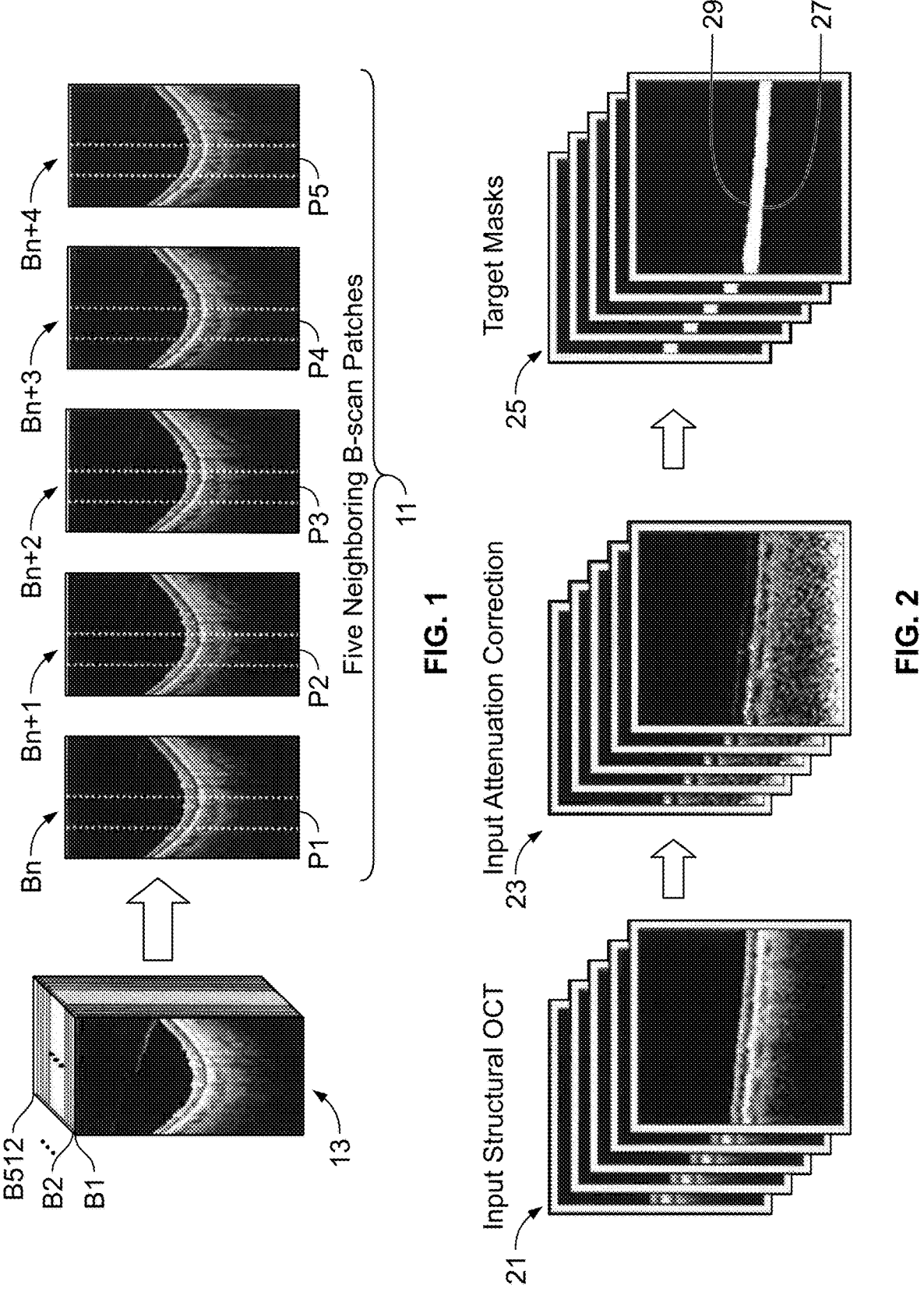
FIG. 1 illustrates a subset of a group of adjacent and neighboring B-scans (or B-scan patches) from a volume scan (or volume patch or C-scan) in accordance with various embodiments.
FIG. 2 illustrates a sequence of an exemplary set of training input patches containing images and a corresponding set of training output (target) masks (patches/images) for the training of a neural network in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not for limitation. Furthermore, any reference to singular includes plural embodiments, and any reference to more than one component or step may include a singular embodiment or step. Also, any reference to attached, fixed, connected, or the like may include permanent, removable, temporary, partial, full, or any other possible attachment option. Additionally, any reference to without contact (or similar phrases) may also include reduced contact or minimal contact. It should also be understood that unless specifically stated otherwise, references to "a," "an" or "the" may include one or more than one, and that reference to an item in the singular may also include the item in the plural. Further, all ranges may include upper and lower values, and all ranges and ratio limits disclosed herein may be combined.

An optical coherence tomography (OCT) system allows the construction of a planar (2D), frontal view (e.g., en face) image of a select part of a tissue volume (e.g., a target tissue slab (sub-volume) or target tissue layer(s), such as the retina of an eye). Examples of other 2D representations (e.g., 2D maps) of ophthalmic data provided by an OCT system may include layer thickness maps and retinal curvature maps. For example, to generate layer thickness maps, an OCT system may use en-face images, 2D vasculature maps of the retina, and multilayer segmentation data. Thickness maps may be based on measured thickness differences between retinal layer boundaries. Vasculature maps and OCT en face images may be generated, for example, by projecting onto a 2D surface a sub-volume (e.g., tissue slab) defined between two-layer boundaries. The projection may use the sub-volume mean, sum, percentile, or other data aggregation methods. Thus, the creation of these 2D representations of 3D volume (or sub-volume) data often relies on the effectiveness of automated segmentation algorithms to identify the layers upon which the 2D representations are based.

Various retinal layer segmentation algorithms may use knowledge-based approaches and machine learning (including deep learning) approaches. Examples of such approaches include: (1) "A method for automated choroidal-scleral interface segmentation in optical coherence tomography," by Homayoun Bagherinia et al., *IOVS* 2019, Volume 60, Issue 9; (2) "Semiautomated Segmentation of the Choroid in Spectral-Domain Optical Coherence Tomography Volume Scans," by Zhihong Hu et al., *IOVS* 2013, Volume 54, Issue 3; (3) "Automated choroid segmentation of SD-OCT volumes using deep learning," by Jonathan D Oakley et al., *IOVS* 2019, Volume 60, Issue 11; (4) "Automatic Segmentation and Visualization of Choroid in OCT with Knowledge Infused Deep Learning," by Huihong Zhang et al., *IEEE Journal of Biomedical and Health Informatics,* 2020; (5) "Choroid segmentation from Optical Coherence Tomography with graph-edge weights learned from deep convolutional neural networks," by Yuanjie Zheng et al., *Neurocomputing*, Volume 237, 10 May 2017, Pages 332-341; (6) "Choroid Segmentation in Optical Coherence Tomography Images Using Deep Learning," by Ruchir Srivastava et al., *ICBME* 2019: 17th *International Conference on Biomedical Engineering*, pp 31-40; (7) "Automatic choroidal segmentation in OCT images using supervised deep learning methods," by Jason Kugelman et al., *Scientific*

*Reports* volume 9, Article number: 13298 (2019); (8) "Semantic Segmentation of the Choroid in Swept Source Optical Coherence Tomography Images for Volumetrics," by Shingo Tsuji et al., *Scientific Reports* volume 10, Article number: 1088 (2020); (9) "Choroid Segmentation of Retinal OCT Images Based on CNN Classifier and 12-1q Fitter," by Fang He et al., *Computational and Mathematical Methods in Medicine,* 2021; and (10) "Attenuation correction assisted automatic segmentation for assessing choroidal thickness and vasculature with swept-source OCT," by Hao Zhou et al., *Biomedical Optics Express*, Vol. 9, Issue 12, pp. 6067-6080 (2018).

The choroid vascular layer which is part of the uvea of the eye is between the Bruch's membrane and the sclera. The dysfunction of the choroid has been implicated in various retinal and choroidal diseases. The identification of pachy-choroid spectrum disorders can be tied in part to the improvements of optical coherence tomography (OCT) technology even though the visibility of choroids is challenging in time or spectral domain OCT. Using enhanced depth imaging OCT can or will improve precision analysis of the morphology and physiology of the choroid, and especially to the choroid-scleral boundary and vasculature. Changes in the choroidal thickness viewed can be related to some ocular conditions such as macular degeneration and myopia. Therefore, the reliable choroidal layer segmentation and analysis have become a useful diagnostic tool for retinal diseases.

In various exemplary embodiments, the present disclosure describes methods and systems directed to processes using deep-learning-based choroidal-scleral interface segmentation methodology (e.g., a deep-learning machine model) with optical coherence tomography (OCT) volumes.

In various exemplary embodiments, an OCT system and/or other ophthalmic imaging systems may be configured with features: A semi-automatic method configured to generate target images (ground truth training images) using a pre-existing multi-retinal segmentation (MLS) algorithm which may mitigate the need for manual segmentation of OCT images for training a machine learning model for choroidal-scleral interface segmentation.

In various embodiments, the method may be configured to be independent of the scan field-of-view (FOV) or scan density by using OCT patches.

In various embodiments, neighboring B-scan patches (of the OCT volume scan) are segmented simultaneously (e.g., using 3D segmentation).

In various embodiments, input patches are configured to train a neural network (NN) and may consist of structural OCT B-scans patches (e.g., training input images/patches) and corresponding attenuation-corrected B-scans patches (e.g., training output images/patches).

In various embodiments, convolutional neural networks (CNNs), U-nets, etc. comprise neural networks (NN) that are based on a discrete cosine transform (DCT), resulting in a unique NN architecture. Unlike other NNs that may include an encoding stage consisting of multiple convolution layers followed by a decoding stage consisting of multiple deconvolution layers, embodiments of the present disclosure describe methods and systems that implement a NN architecture that omits the use of deconvolution layers. Instead, the decoding stage comprises one (or more) DCT layers.

In various embodiments, the present disclosure describes methods and systems that enable uncertainty detection of the segmented regions (e.g., a neural network/layer) to identify segmented regions having low segmentation confidence (multi-task network or postprocessing classification methods can be used for uncertainty detection). The neural network/layer examines the initial choroid-scleral layer segmentation provided by the present NN and uses knowledge of the general shape of a choroid-scleral layer to identify and exclude from the initial choroid-scleral layer segmentation any patch regions deemed inconsistent with (e.g., deviate from) the expected typical shape of a choroid-scleral layer. For example, the neural network classifier layers (classification module) may remove patches/parts of the initial choroid-scleral layer segmentation that contradict a defined smooth curvature or a predefined library of acceptable shapes.

In various exemplary embodiments, the present disclosure describes methods and systems that enable choroid-scleral interface modeling (e.g., polynomial, Zernike, Gridfit, etc.), to determine if part of the initial choroid-scleral layer segmentation deviates from an expected shape model (e.g., smoothness) to identify path regions to be removed.

In various exemplary embodiments, the present disclosure describes methods and systems directed to choroid-scleral interface segmentation processes based on a supervised deep-learning algorithm. In the implementation, deep learning methods require training data which includes training example sets of input images with corresponding output target images.

In various exemplary embodiments, the present disclosure describes methods and systems that use multi-retinal segmentation (MLS) to generate target images (masks) for input images. The target mask (ground truth) is the region between the retinal pigment epithelium (RPE) retina layer (or any other retinal layer) and the choroid-scleral interface.

Referring to FIG. 1, FIG. 1 illustrates a diagram 100 of an input set 11 of adjacent and neighboring B-scans (or B-scan patches) obtained from a volume scan (or volume patch or C-scan) 13. Volume scan 13 may comprise a set of multiple adjacent B-scans. Volume scan 13 comprises a set of 512 individual B-scans, B1 to B512 scans. To configure the input set 11 of adjacent and neighboring B-scans, a predefined number of neighboring B-scans are selected (e.g., five B-scans identified as a set of Bn, Bn+1, Bn+2, Bn+3, and Bn+4) from volume scan 13 Which, a B-scan patch is then defined from each B-scan to configure an input set 11 that comprise a set of adjacent patches. For example, five neighboring 3 mm (0.1181 inch) OCT patches P1, P2, P3, P4, and P5 (identified as the region between a pair of white dotted lines 5) are respectively extracted/defined from the five neighboring OCT B-scans (Bn, Bn+1, Bn+2, Bn+3, and Bn+4), and the patches are segmented simultaneously. The input set 11 may be used to defined training input images/patches for training the neural network or to define input sets for submission to an already trained neural network, as discussed below.

Referring to FIG. 2, FIG. 2 illustrates the creation of a set of training input patches/images 23 and a corresponding set of training output (target) masks (patches/images) 25 for the training of a neural network in accordance with various embodiments The set of input images/patches to the neural network consists of multiple OCT structural patches 21 (e.g., like patches P1-P5 of FIG. 1) with the corresponding attenuation corrected patches 23. For example, the input patch 21 may be attenuation corrected by removing vessel/AMD shadows and improving contrast. More information for input attenuation correction is provided in "Attenuation correction assisted automatic segmentation for assessing choroidal thickness and vasculature with swept-source OCT," Hao Zhou et al., *Biomedical Optics Express* Vol. 9, Issue 12, pp. 6067-6080 (2018), herein incorporated in its entirety by reference. A corresponding output training target mask/image 25 (with appropriate choroid-scleral layer segmentation 27) may be defined from each input patch 21 or attenuation-corrected patch 23.

For example, each training output target image 25 may have the boundary between a select upper retinal layer 29 (e.g., RPE layer or other retinal layers, as reference) and the desired choroid-scleral layer (lower boundary layer 27) as the lower retinal layer. The objective of the present machine model is to segment the lower boundary layer 27, which defines the choroid-scleral (or choroid) layer of the eye. The upper boundary (upper retinal layer 29) may optionally be disregarded after choroid-scleral segmentation. It is noted, however, that the number of output target images (masks) 25 is equal to the number of OCT structural patches 21 with one-to-one correspondences. In the present example, multiple neighboring B-scans/patches are provided to define 3D (patch) data, which defines a high correlation at the choroid region. Using this 3D data enforces continuity between the adjacent choroid-scleral segmentations in adjacent B-scan patches.

In various exemplary embodiments, a training set (comprised of a large number of OCT patches) is extracted from hundreds of OCT volume scans of various field-of-views (FOVs), such as 3 mm (0.1181 inch)×3 mm (0.1181 inch), 6 mm (0.2362 inch)×6 mm (0.2362 inch), 9 mm (0.3543 inch)×9 mm (0.3543 inch), 12 mm (0.4724 inch)×12 mm (0.4724 inch), 15 mm (0.5906 inch)×9 mm (0.3543 inch). The patches with wrong or incorrect retinal pigment epithelium (RPE) and choroid segmentations (as determined using multi-retinal layer segmentation (MLS)) may optionally be removed from the training set. The patches may be turned around the axial direction to mimic the other eye (e.g., from left eye to right eye) as a type of augmentation method.

In various exemplary embodiments, a novel neural network architecture based on one or more discrete cosine transform (DCT) decoders (e.g., a DCT network) is configured to train a machine model using the training data described.

Figures 3A, 3B:
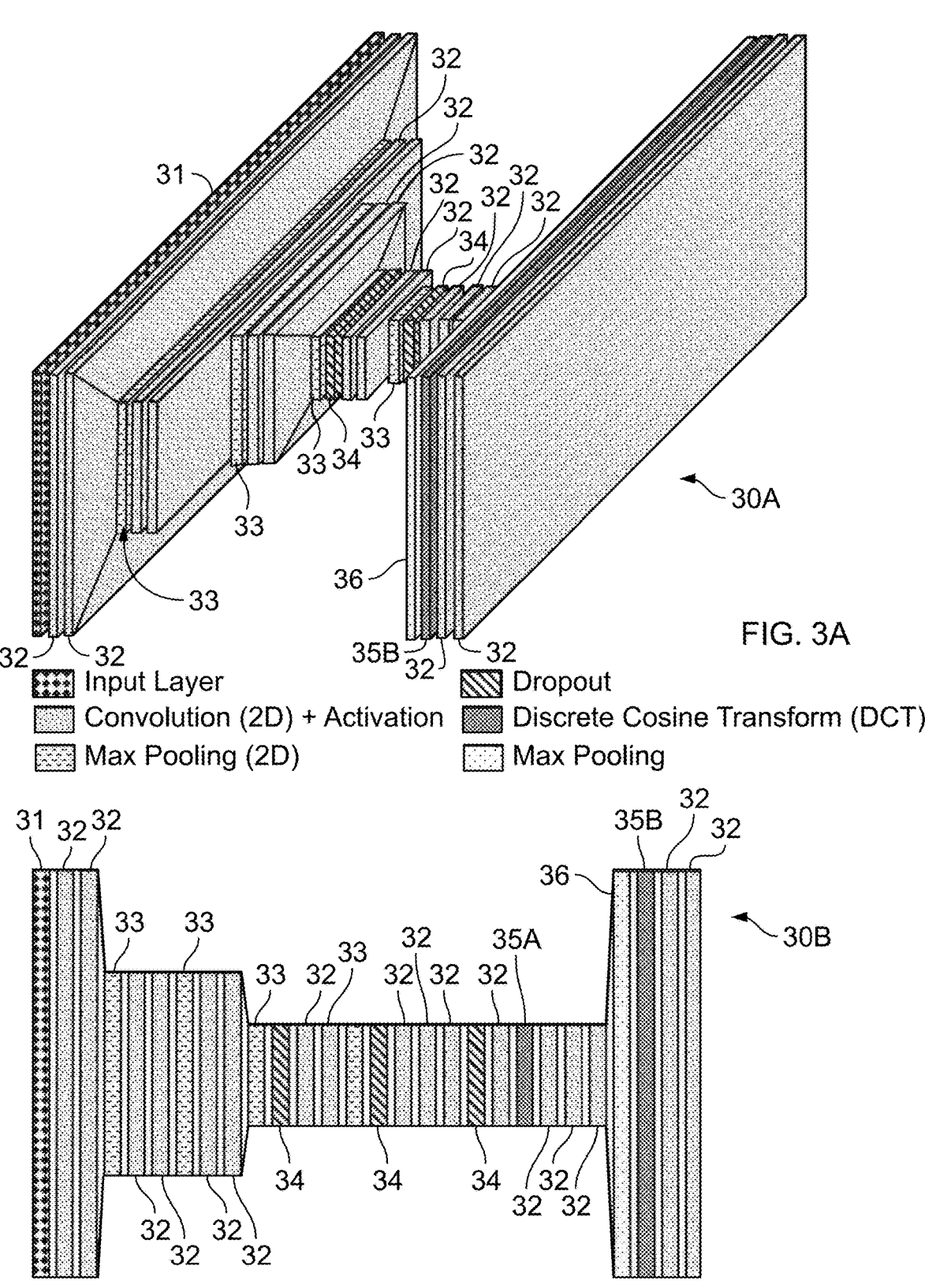
FIG. 3A illustrates a diagram of an oblique view of a DCT-network architecture in three dimensions (3D) and two dimensions (2D) in accordance with various embodiments.
FIG. 3B illustrates a diagram of a lateral view of a DCT-network architecture in three dimensions (3D) and two-dimensions (2D) in accordance with various embodiments.

Referring to FIGS. 3A and 3B, FIGS. 3A and 3B illustrate a set of diagrams of different views of a DCT-network architecture in three-dimensions (3D) 30A and two-dimensions (2D) 30B in accordance with various embodiments.

In various embodiments, the DCT-network architecture may consist of two parts: a first encoder part (e.g., an encoder path or contracting path, at the front end) and a decoder part (e.g., a decoder path or expanding path) at the back end (following the decoder path). In the implementation, these features are configured of an input layer 31 that receives the OCT image data segmented into one or more input sets and sent or transferred to the encoder part of the network, which is configured in the first half with autoencoder features. The layout of the encoder vis a vis the encoder path uses two convolution layers 32 (including ReLU-nonlinearity, e.g., activation, or other activation function known in the art) that are configured in a 3×3 Filter size, followed by maximum pooling function (e.g., max pooling (2D) 33. Interspersed between the two convolution layers 32 are one or more dropout layers 34 configured with a dropout rate in a range of about 0.1 (10 percent) to 0.4 (40 percent). Pooling (MaxPool-Layers) determines the bottleneck size of the encoder. This size may reflect the energy distribution of the discrete cosine transform of the training labels (e.g., labeled training set). For example, the choroid masks (or target masks discussed in reference to FIG. 2) may have energy (L2-norm regulation) concentrated in the 32×32 low-frequency area, so an appropriate bottleneck size, in the present example, is selected as 32×32 pixels.

In various exemplary embodiments, after the encoder operation (encoder path), the subsequent step is the decoder operation (decoder path). The initial step in the decoder (decoder operation) is applying an inverse cosine transform (in accordance with the bottleneck size). In the implementation, a frequency transformation is followed by processing through multiple (e.g., three) convolutional layers that consist of 1×1, 1×1, and 3×3 filter sizes (e.g., those layers combine different channels). The penultimate layers are zero-padding layers (to expand/grow the size of the image being processed from the bottleneck size to the original image size (e.g., the input image)) combined with a discrete cosine transform. The zero-padding layers precede this DCT. The last layers apply a rectified linear activation function (ReLU) and a sigmoid function (tanh).

The decoder part/path of the network has two custom layers: A DCT (2D) layer includes a first DCT (2D) layer 35A that computes the 2D (inverse) discrete cosine transform (orthogonal, type II) of the layer input, and a second DCT (2D) layer 35B that provides the 2D discrete cosine transform. The format of the input tensor is assumed to be batch size, height, width, and channels, and the discrete cosine transform is computed along the innermost two dimensions (height, and width). The zero-padding layer 36 pads the bottleneck image to the original input image size. Padding is done by appending zeros to the innermost dimensions of the layer-input tensor. This padding combined with the 2D-DCT transform leads to image up-sampling.

The model was trained with a simple mean squared error as initialization. After this initialization phase, the loss was switched to a boundary loss function. This boundary loss was defined as the weighted sum of two terms:

Symmetric dice loss (e.g., Sørensen-Dice coefficient, or other known similarity coefficients, e.g., a statistic used to gauge the similarity of two samples): This is a pixel-wise loss defined as the average of the dice-loss of the segmentation plus the dice loss of the inverse segmentation (1-segmentation). The dice loss is defined as:

dice $$(a, b) := 1 - \frac{2 * \sum a_i b_i + 1}{\sum a_i + \sum b_i}$$

where a is ground truth and b is the predicted image (e.g., output segmentation image), or vice versa.

Boundary regularization: To make the network output more sensitive to the boundary of the ground truth mask a special regularization was used. First, the boundary of the network output was extracted using the height-gradient norm (dz×dz'), where dz may be the gradient of the image in the Z, or axial, direction, and dz' may be the transpose (e.g., of the vector). For a (mostly) binary image this result in another binary image 1 at the object boundary and 0 elsewhere. This boundary image is then multiplied by the absolute value of the signed Euclidian distance transform of the ground truth segmentation. For a binary gradient image, this replaces the 1's with the distance of this pixel to the boundary. Finally, the mean is calculated. With length normalization this mean would correspond to the average boundary distance of the network output to the ground truth mask boundary.

The configured machine model is used to segment the region between RPE (or other selected retinal layer) and choroid-sclera interface of OCT volume test patches of 3 mm (0.1181 inch). The OCT patches can have regions that the network has never seen before. Therefore, the segmentation of such regions usually is incorrect. An uncertainty algorithm (e.g., neural network classification module/process/layer) can exclude the regions with wrong segmentation. The uncertainty of a patch region is a classification problem. This classification problem can be solved using methods such as: an existing classification network, a multitask network to train and predict the segmentation and uncertainty with a knowledge-based postprocessing approach by using the choroid-scleral interface attributes such as a smooth surface with a low-frequency part. For example, the error between the choroid-scleral interface in a patch to the linear fit can be a metric to determine if a region of a patch is segmented incorrectly.

Figures 4A, 4B:
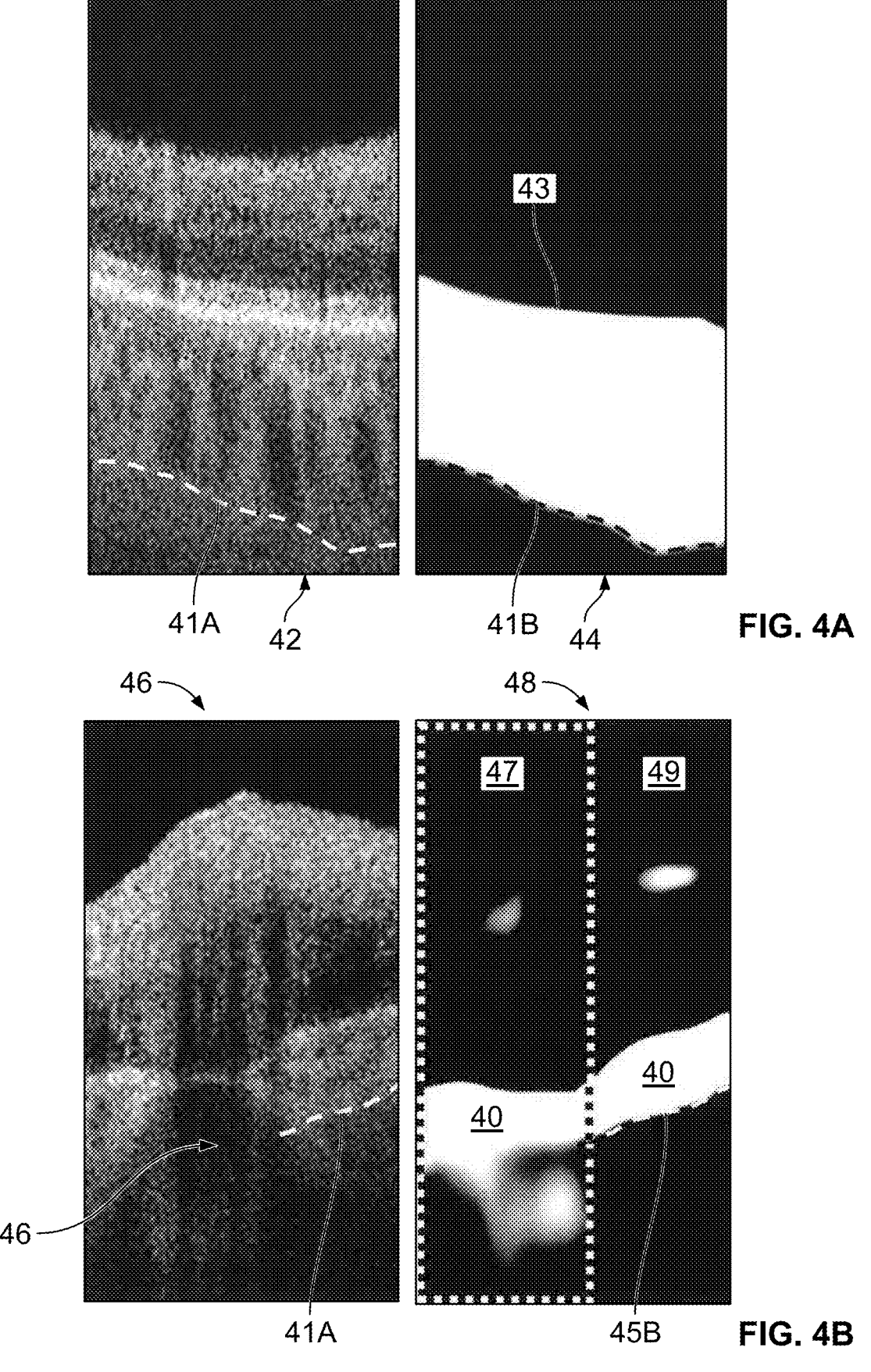
FIG. 4A shows a set of images of a correct choroid-scleral segmentation of a first input patch in accordance with various embodiments.
FIG. 4B shows a set of images of incorrect segmentation of a second input patch in accordance with various embodiments.

Referring to FIG. 4A, FIG. 4A illustrates a correct choroid-scleral segmentation 44 of a first input patch 42 and FIG. 4B illustrates an incorrect segmentation of a second input patch 42. In the present example, the first input patch 42 is like the training images used to train the present neural network, and the resultant machine model produces a correctly segmented image 44. Dash line 41A indicates the choroid-scleral segmentation in the first input patch 42, and segmented output image 44 shows the correct choroid-scleral segmentation 41 Band shows an upper boundary 43 representatives of the RPE layer, in the present example. However, an objective of the present machine model is to identify the choroid-scleral segmentation, and the lower boundary region (the correct choroid-scleral segmentation 41B) is of particular interest. FIG. 4B provides an example of what may happen if the input image to the present machine model resembles none of the images used to train the present machine model. This may occur, for example, if a captured/acquired OCT volume scan suffers from image artifacts that the present machine model has not been trained to recognize, or if the choroid-scleral boundary is not found within the acquired/captured OCT volume scan, or if the machine model has not been trained to recognize a captured type of choroidal region.

In the example of FIG. 4B, the second input patch 46 shows the type of choroidal region never seen by the neural network (e.g., resembles none of the training images used to train the neural network). A part 45A of the choroidal-scleral layer resembles the types of training image used, but another part (second input patch 46) is not easily recognizable by the present machine model. The second segmented output image 48 has a first region 49 with a correctly segmented choroid-scleral region 45B and a second region 47, enclosed within a dotted box, with an incorrectly segmented choroidal-scleral section, noted as the lower part/boundary of the white segmentation 40. Here, the uncertainty algorithm (e.g., neural network classification module/process/layer) may apply a smoothness test to the lower boundary of the white segmentation 40 to identify where the lower boundary deviates from an expected/known general shape of a choroid-scleral layer. This detection may also be done by comparison with a library of acceptable shapes, or by the above-described methods. In this manner, bad region 47 and good region 49 are identified, and bad region 47 is removed from the second segmented output image 48. This test may be applied in multiple dimensions (e.g., 2D) by comparing a choroid-scleral segmentation of a current OCT patch with that from an adjunct/neighboring OCT patch.

In various embodiments, the choroid-scleral interface of the OCT volume can be modeled using polynomial fitting or Zernike fitting. The polynomial fitting interpolates/extrapolates the excluded regions (e.g., region 47 due to uncertainty) to create a complete 2D surface. A more general approach is the Gridfit (a grid fitting tool) or thin plate spline which interpolates/extrapolates the data smoothly across the scan field-of-view (FOV).

Referring to FIG. 5A, FIG. 5A illustrates a 2D choroid-scleral map 51 with removed (bad) regions of uncertainty 53, shown as darkened rectangles, and FIG. 5B illustrates the filling in of the removed regions of uncertainty 53 from FIG. 5A, such as by interpolates/extrapolates, to produce a corrected 2D choroid-scleral map 55. In the present example, 2D choroid-scleral map 51 shows a choroid surface network output plus outlier detection (e.g., removal of bad regions of uncertainty 53 shown as dark/black rectangular regions). Also shown is the optic nerve head (ONH) region 57, which does not have a choroid layer, and results in an enlarged dark region 57. 2D choroid-scleral map 55 fills in all the dark regions to produce a smooth choroid surface.

Figure 6B:
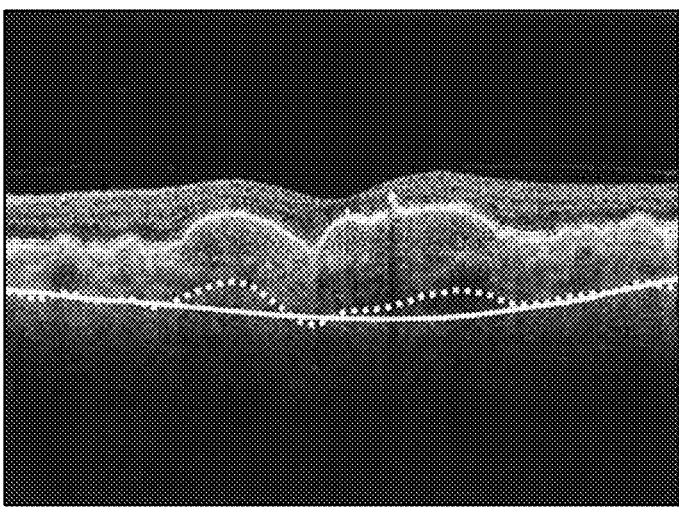
Figure 6C:
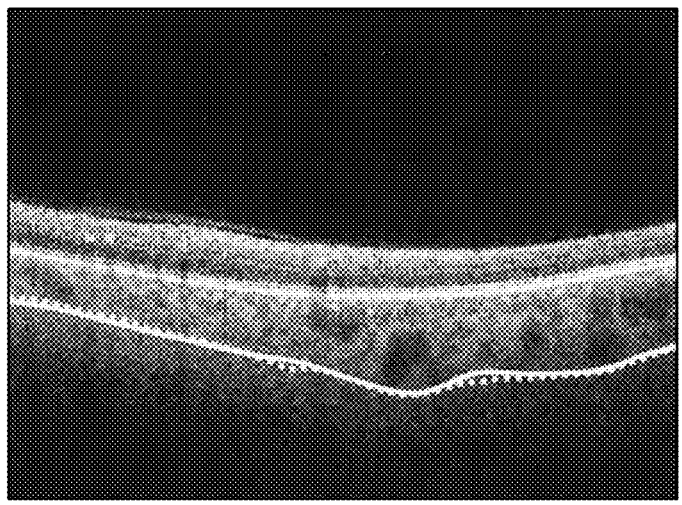
Figure 6D:
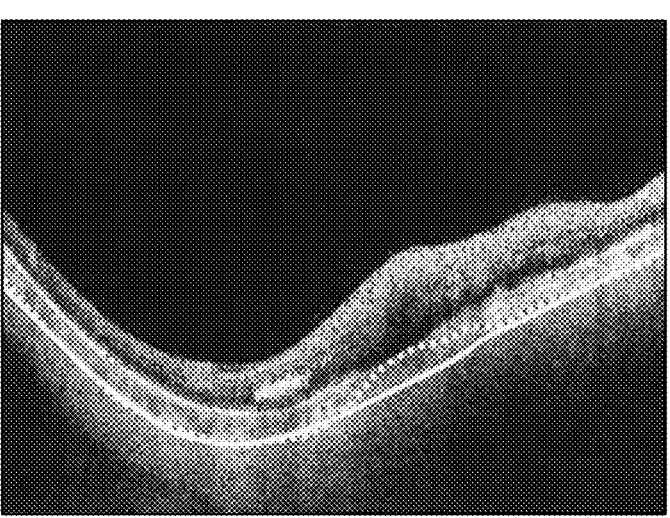
Figure 6E:
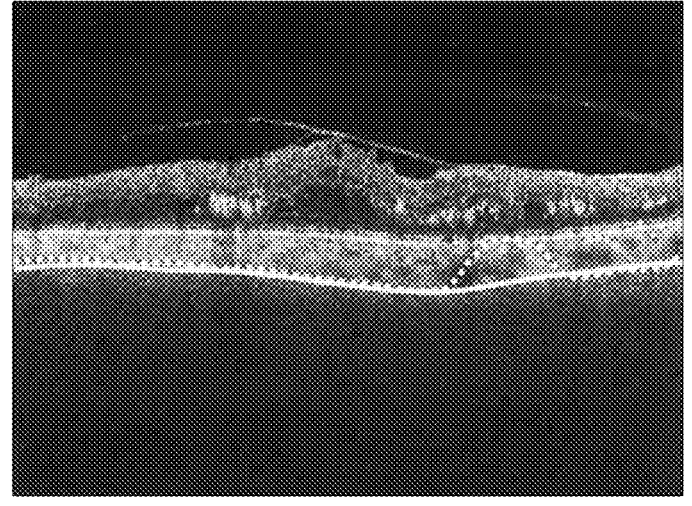
Figure 6F:
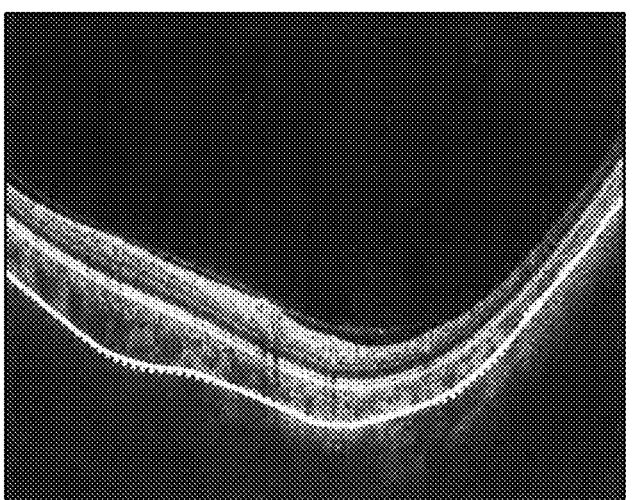

FIGS. 6A, 6B, 6C, 6D, 6E, and 6F illustrate a set of examples of OCT B-scans with choroid-scleral interface computed by MLS (white dotted line) and the described MLS (white solid line). As shown, the present disclosure describes a preferred and correct choroid-scleral segmentation. FIG. 6A shows a 3 mm×3 mm FOV. FIG. 6B shows a 6 mm (0.2362 inch)×6 mm (0.2362 inch) FOV. FIG. 6C shows a 9 mm×9 mm FOV. FIG. 6D shows a 12 mm (0.4724 inch)×12 mm FOV. FIG. 6A shows a 15 mm (0.5906 inch)×9 mm (0.3543 inch) FOV. FIG. 6A shows a 15 mm (0.5906 inch)×15 mm (0.5906 inch) FOV. In various exemplary embodiments, the present disclosure as described provides a system or method for use with an optical coherence tomography (OCT) system that segments a choroid-scleral layer from a volume scan (OCT image data) of an eye.

Referring to FIG. 7, FIG. 7 illustrates an exemplary workflow 70 of the present system. The workflow 70 first begins with collecting the OCT image data (volume scan) of the eye, such as from an OCT system, at step 71. The OCT image data may be collected from an existing library of OCT images or may be actively acquired with an OCT system/device, such as discussed below. The acquired OCT data is then submitted to a deep learning machine model (at step 73), which is preferably based on a neural network, to produce an initial choroid-scleral layer segmentation. The neural network is characterized by having a contracting (encoding) path having multiple convolution layers followed by a max pooling layer, and an expanding (decoding) path following the contracting path, where the expanding path has at least one discrete cosine transform (DCT) decoder.

In various exemplary embodiments, the neural network may have two or more DCTs, a first DCT that receives encoded data from the encoding path, and applies an inverse discrete cosine transfer to the received encoded data. The second DCT provides a discrete cosine transform to provide decoded data to a pair of more convolution layers and produces the initial choroid-scleral layer segmentation. The initial choroid-scleral layer segmentation is then submitted to uncertainty detection (e.g., authentication module and neural network classification module/steps) to identify and exclude, from the initial choroid-scleral layer segmentation, patch regions considered to have a shape inconsistent with that of known choroid-scleral layers (at step 75). A 2D choroid scleral layer map may then be defined from the initial choroid-scleral layer segmentation with the missing regions. At step 77, final or post proceeding step is configured to fill in the missing regions, such as by interpolation, and to define a final choroid-scleral layer segmentation. In various implementations, the missing regions may be filled in by polynomials, Zernike, or Gridfit.

Hardware and Architecture:

Fundus Imaging System

In various exemplary embodiments, two categories of imaging systems may image the fundus and include a flood illumination imaging system (or flood illumination imager) and a scan illumination imaging system (or scan imager). The Flood illumination imager operates by flooding light across an entire field of view (FOV) of interest to a specimen at once, by using a flash lamp that enables the capture of a full-frame image of the specimen (e.g., the fundus) with a full-frame camera (e.g., a camera having a two-dimensional (2D) photosensor array of sufficient size to capture the desired FOV).

For example, a flood illumination fundus imager would flood the fundus of an eye with light, and capture a full-frame image of the fundus in a single image capture sequence of the camera. A scan imager provides a scan beam scanned across a subject, e.g., an eye, and the scan beam is imaged at different scan positions as it is scanned across the subject creating image segments that may be reconstructed, e.g., montaged, to create a composite image of the desired FOV. The scan beam could be a point, a line, or a two-dimensional area such as a slit or broad line. An example of a fundus imager is described in U.S. Pat. No. 8,967,806, entitled FUNDUS CAMERA WITH STRIP-SHAPED PUPIL DIVISION, AND METHOD FOR RECORDING ARTIFACT-FREE, HIGH-RESOLUTION FUNDUS IMAGES, filed on Nov. 4, 2011, assigned to Carl Zeiss Jena and U.S. Pat. No. 8,998,411, entitled LIGHT FIELD CAMERA FOR FUNDUS PHOTOGRAPHY, filed on Jul. 5, 2012, assigned to Carl Zeiss Meditec Inc, both of which are incorporated in their entirety by reference.

Figure 8:
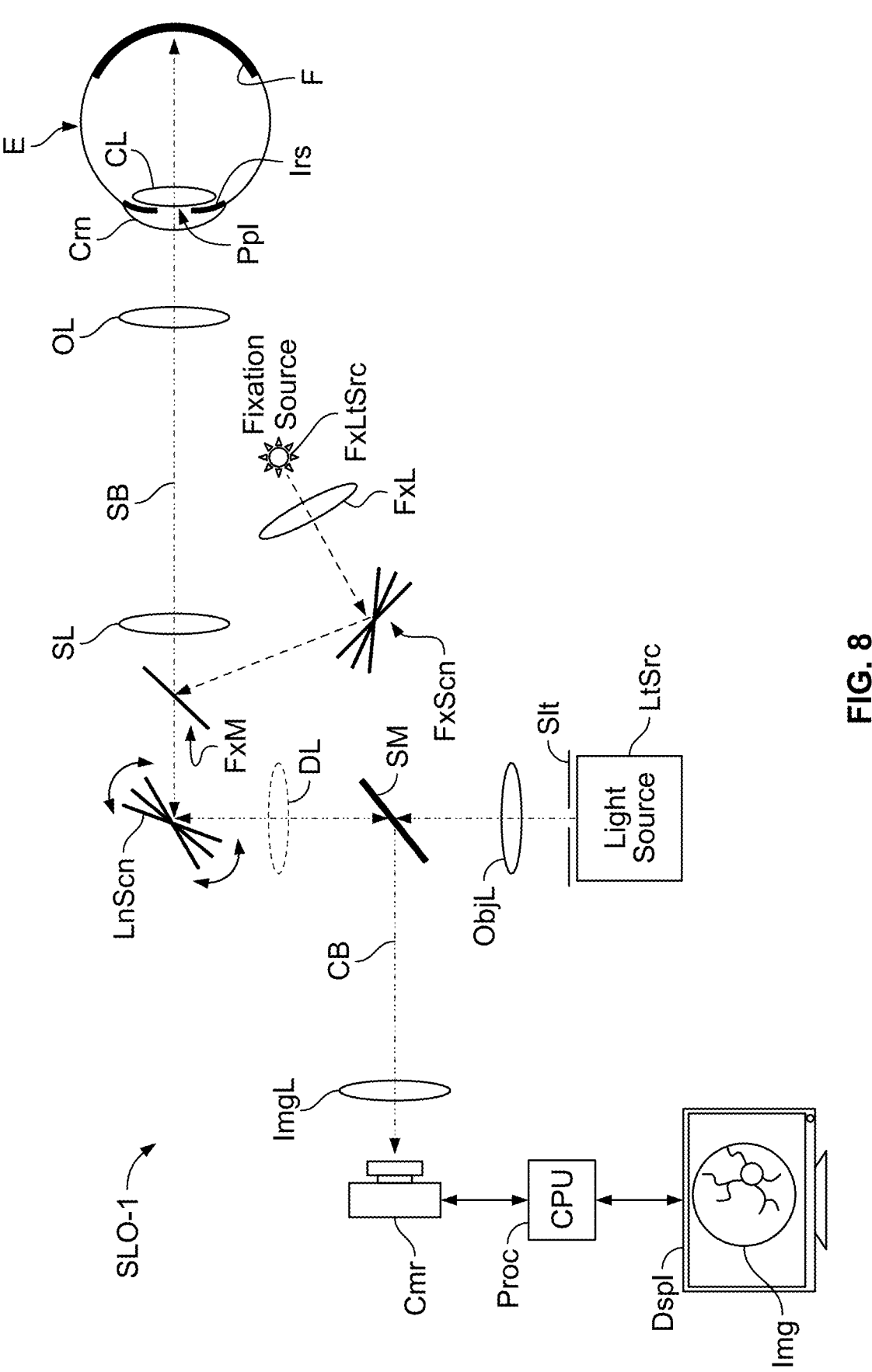
FIG. 8 illustrates an exemplary diagram of a slit-scanning ophthalmic system for imaging a fundus in accordance with various embodiments.

Referring to FIG. 8, FIG. 8 illustrates a diagram of an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical parts of the eye E (including the cornea Cm, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may adjust the width of the scanning line beam SB. Also, slit Slt may remain static during imaging or may be adjusted to different widths to allow for different confocality levels and different applications either for a particular scan or during the scan for suppressing reflexes.

An optional objective lens ObjL may be placed in front of the slit Slt. The objective lens ObjL can be any of modern lenses including but not limited to refractive, diffractive, reflective, or hybrid lenses/systems. The light from slit Slt passes through a pupil-splitting mirror SM and is directed towards a scanner LnScn. It is desirable to bring the scanning plane and the pupil plane as near together as possible to reduce vignetting in the system. Optional optics DL may be included to manipulate the optical distance between the images of the two parts. Pupil splitting mirror SM may pass an illumination beam from light source LtSrc to scanner LnScn, and reflect a detection beam from scanner LnScn (e.g., reflected light returning from eye E) toward a camera Cmr. A task of the pupil-splitting mirror SM is to split the illumination and detection beams and to aid in the suppression of system reflexes.

The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in U.S. Pat. No. 9,456,746, which is herein incorporated in its entirety by reference.

From the scanner LnScn, the illumination beam passes through one or more optics, a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles) and produces a scanning line beam SB with a substantially flat surface focal plane (e.g., a collimated light path). Ophthalmic lens OL may then focus the scanning line beam SB onto an object to be imaged. In the present example, the ophthalmic lens OL focuses the scanning line beam SB onto the fundus F (or retina) of eye E to image the fundus. In this manner, scanning line beam SB creates a traversing scan line that travels across the fundus F. One possible configuration for these optics is a Kepler-type telescope wherein the distance between the two lenses is selected to create an about telecentric intermediate fundus image (4-f configuration).

The ophthalmic lens OL could be a single lens, an achromatic lens, or an arrangement of different lenses. All lenses could be refractive, diffractive, reflective, or hybrid as known to one skilled in the art. The focal length(s) of the ophthalmic lens OL, scan lens SL, and the size and/or form of the pupil splitting mirror SM and scanner LnScn could be different depending on the desired field of view (FOV), and so an arrangement in which multiple parts can be switched in and out of the beam path, for example by using a flip in optic, a motorized wheel, or a detachable optical element, depending on the field of view can be envisioned.

Since the field of view change results in a different beam size on the pupil, the pupil splitting can also be changed with the change to the FOV. For example, a 45° to 60° field of view is a typical, or standard, FOV for fundus cameras. Higher fields of view, e.g., a widefield FOV, of 60°-120°, or more, may also be possible. A widefield FOV may be desired for the Broad-Line Fundus Imager (BLFI) with other imaging modalities such as optical coherence tomography (OCT). The upper limit for the field of view may be determined by the accessible working distance combined with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E is illuminated. Reflected or scattered light (or emitted light in the case of fluorescence imaging) is directed back along a similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. Scanner LnScn scans the illumination beam from pupil-splitting mirror SM to define the scanning illumination beam SB across eye E, but since scanner LnScn also receives returning light from eye E at the same scan position, scanner LnScn descends the returning light (e.g., canceling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image.

An imaging (e.g., objective) lens ImgT may be positioned in the detection path to image the fundus to the camera Cmr. As for objective lens ObjL, imaging lens ImgL may be any lens known in the art (e.g., refractive, diffractive, reflective, or hybrid lens). Additional operational details ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system of FIG. 17). Thus, the collection beam (returning from all scan positions of the scanning line beam SB) is collected by the camera Cmr, and a full-frame image Img may be constructed from a composite of the individually captured collection beams, such as by montaging. However, other scanning configurations are also contemplated, including ones where the illumination beam is scanned across the eye E and the collection beam is scanned across a photosensor array of the camera. PCT Publication WO 2012/059236 and US Patent Publication No. 2015/0131050 (issued U.S. Pat. No. 9,456,746), herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dspl, both of which can be part of the imaging system itself, or maybe part of separate, dedicated processing and/or displaying unit(s), such as a computer system wherein data is passed from the camera Cmr to the computer system over a cable or computer network including wireless networks. The display and processor can be an all-in-one unit. The display can be a traditional electronic display/screen or of the touch screen type and can include a user interface for displaying information to and receiving information from an instrument operator or user. The user can interact with the display using any user input device as known in the art including, but not limited to, a mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 8. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is positioned such that it is at the pupil plane of the system so the light pattern on the retina/fundus can be moved depending on the desired fixation location.

Slit-scanning ophthalmoscope systems can operate in different imaging modes depending on the light source and wavelength-selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel best highlights the choroid, the green channel highlights the retina, and the blue channel highlights the anterior retinal layers. Also, the light at specific frequencies (e.g., individual-colored LEDs or lasers) can excite different fluorophores in the eye (e.g., autofluorescence) and the resulting fluorescence can be detected by filtering out the excitation wavelength.

The fundus imaging system can also provide an infrared reflectance image, such as by using an infrared laser (or other infrared light sources). The infrared (IR) mode is useful because the eye is not sensitive to the IR wavelengths. This may permit a user to continuously take images without disturbing the eye (e.g., in a preview/alignment mode) to aid the user during the alignment of the instrument. Also, the IR wavelengths have increased penetration through tissue and may provide improved visualization of choroidal structures. In addition, fluorescein angiography (FA) and indocyanine green (ICG) angiography imaging can be done by collecting images after a fluorescent dye has been injected into the bloodstream. For example, in FA (and/or ICG) time-lapse images may be captured after injecting a light-reactive dye (e.g., fluorescent dye) into a subject's bloodstream. It is noted that care must be taken since the fluorescent dye may lead to a life-threatening allergic reaction in a part of the population. High contrast, greyscale images are captured using specific light frequencies selected to excite the dye. As the dye flows through the eye, many parts of the eye are made to glow brightly (e.g., fluoresce), making it possible to discern the progress of the dye, and hence the blood flow, through the eye.

Optical Coherence Tomography Imaging System

Optical coherence tomography (OCT) uses low-coherence light to produce two-dimensional (2D) and three-dimensional (3D) internal views of biological tissue. OCT enables in vivo imaging of retinal structures. OCT angiography (OCTA) produces flow information, such as vascular flow from within the retina. Examples of OCT systems are provided in U.S. Pat. Nos. 6,741,359 and 9,706,915, and examples of an OCTA system may be found in U.S. Pat. Nos. 9,700,206 and 9,759,544, which are herein incorporated in their entirety by reference. An exemplary OCT/OCTA system is provided herein.

Figure 9:
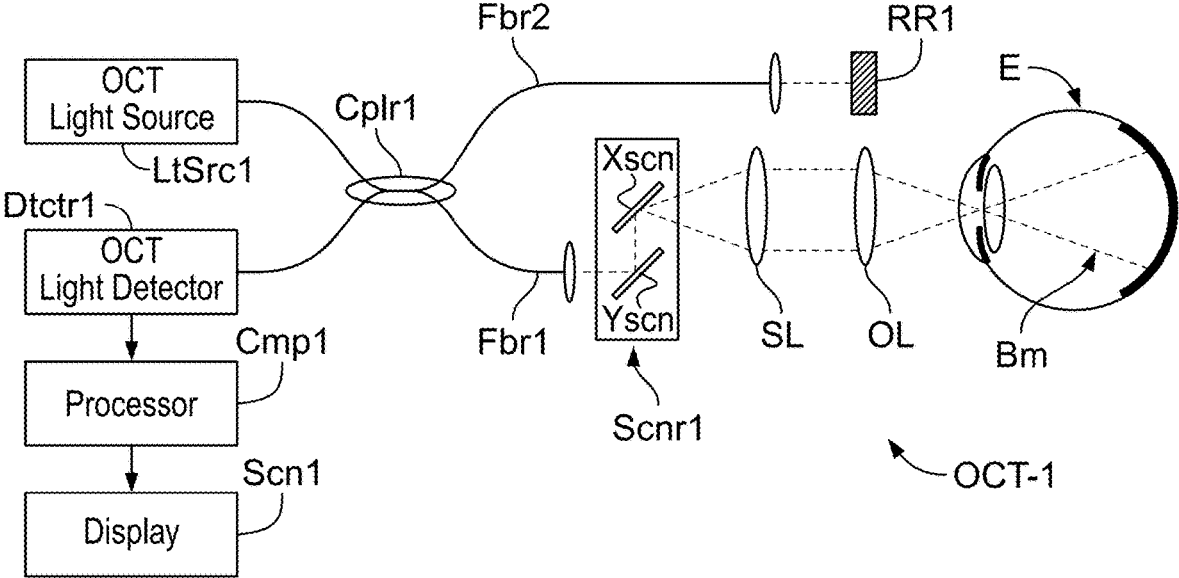
FIG. 9 illustrates a diagram of a frequency domain optical coherence tomography system used to collect 3D image data of the eye for accordance with various embodiments.

Referring to FIG. 9, FIG. 9 illustrates a generalized frequency domain optical coherence tomography (FD-OCT) system used to collect 3D image data of the eye suitable for use with the present invention. An FD-OCT system OCT_1 includes a light source, LtSrc1. Typical light sources include but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 may, for example, be a broadband light source with short temporal coherence length in spectral domain OCT (SD-OCT) or a wavelength tunable laser source in swept source OCT (SS-OCT).

The light may be scanned, with a scanner Scnr1 between the output of the optical fiber Fbr1 and the sample E, so the beam of light (dashed line Bm) is scanned laterally over the region of the sample to be imaged. The light beam from scanner Scnr1 may pass through a scan lens SL and an ophthalmic lens OL and be focused onto the sample E being imaged. The scan lens SL may receive the beam of light from the scanner Scnr1 at multiple incident angles and produce substantially collimated light, and the ophthalmic lens OL may then focus onto the sample.

The present example illustrates a scan beam that needs to be scanned in two lateral directions (e.g., in x and y directions on a Cartesian plane) to scan a desired field of view (FOV). An example of this would be a point-field OCT, which uses a point-field beam to scan across a sample. Scanner Scnr1 is illustratively shown to include two sub-scanners: a first sub-scanner Xscn for scanning the point-field beam across the sample in a first direction (e.g., a horizontal x-direction); and a second sub-scanner Yscn for scanning the point-field beam on the sample in traversing second direction (e.g., a vertical y-direction). If the scan beam were a line-field beam (e.g., a line-field OCT), which may sample an entire line part of the sample at a time, then only one scanner may be needed to scan the line-field beam across the sample to span the desired FOV. If the scan beam were a full-field beam (e.g., a full-field OCT), no scanner may be needed, and the full-field light beam may be applied across the entire, desired FOV at once.

Despite the beam used, light scattered from the sample (e.g., sample light) is collected. In the present example, scattered light returning from the sample is collected into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, for example, in a fiber coupler Cplr1, to form light interference in an OCT light detector Dtctr1 (e.g., photodetector array, digital camera, etc.).

Although a single fiber port is shown going to the detector Dtctr1, those skilled in the art will recognize that various designs of interferometers can be used for balanced or unbalanced detection of the interference signal. The output from the detector Dtctr1 is supplied to a processor (e.g., internal or external computing device) Cmp1 that converts the interference seen into depth information of the sample.

The depth information may be stored in a memory associated with the processor Cmp1 and/or displayed on a display (e.g., computer/electronic display/screen) Scn1. The processing and storing functions may be localized within the OCT instrument, or functions may be offloaded onto (e.g., performed on) an external processor (e.g., an external computing device), to which the collected data may be transferred.

Figure 17:
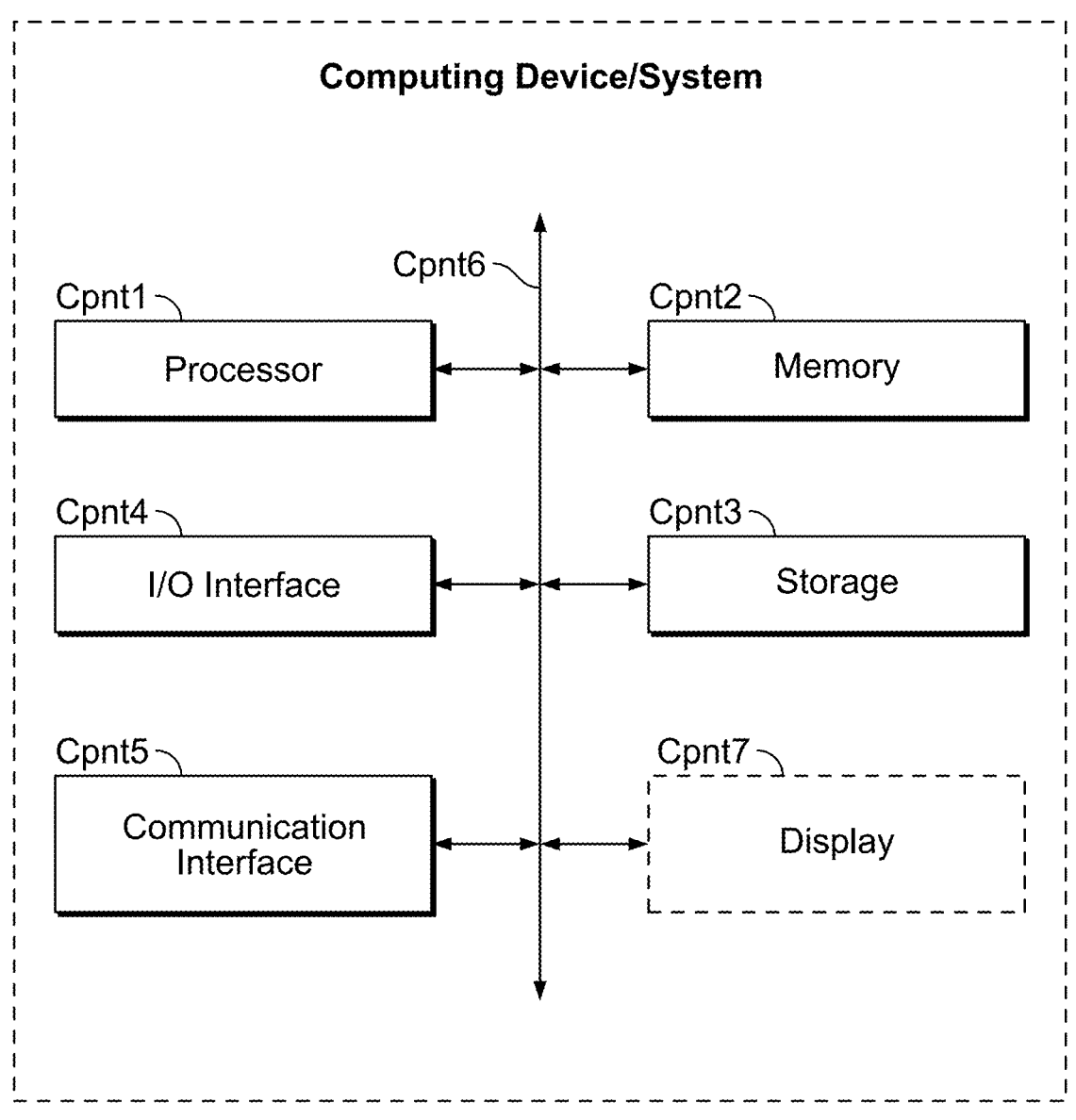
FIG. 17 illustrates a diagram of an example computer system (or computing device or computer) in accordance with various embodiments.

In various embodiments, an example of a computing device (or computer system) is shown in FIG. 17. The computing device (or processor) can be dedicated to data processing or perform other tasks quite general and not dedicated to the OCT device. The processor (computing device) Cmp1 may include, for example, a field-programmable gate array (FPGA), a digital signal processor (DSP), an application-specific integrated circuit (ASIC), a graphics processing unit (GPU), a system-on-chip (SoC), a central processing unit (CPU), a general purpose graphics processing unit (GPGPU), or a combination thereof, that may perform some, or the entire, processing steps in a serial and/or parallelized fashion with one or more host processors and/or one or more external computing devices.

The sample and reference arms in the interferometer could consist of bulk-optics, fiber-optics, or hybrid bulk-optic systems and could have different architectures such as Michelson, Mach-Zehnder, or common-path-based designs as known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—Holographic Optical Coherence Tomography," *Optics Letters,* 36(13): 2390 2011; Y. Nakamura, et al, "High-Speed Three Dimensional Human Retinal Imaging by Line Field Spectral Domain Optical Coherence Tomography," *Optics* Express, 15(12):7103 2007; Blazkiewicz et al, "Signal-To-Noise Ratio Study of Full-Field Fourier-Domain Optical Coherence Tomography," *Applied Optics,* 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described could be applied to any OCT system. Various aspects of the invention could apply to any OCT system or other types of ophthalmic diagnostic systems and/or multiple ophthalmic diagnostic systems including but not limited to fundus imaging systems, visual field test devices, and scanning laser polarimeters.

In various embodiments, in Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram results in a complex-valued OCT signal output $Aj(z)=|Aj|e^{i\varphi}$. The absolute value of this complex OCT signal, $|Aj|$, reveals the profile of scattering intensities at different path lengths, and scattering as a function of depth (z-direction) in the sample. Similarly, the phase, $\varphi j$ can also be extracted from the complex-valued OCT signal. The profile of scattering as a function of depth is called an axial scan (A-scan).

In various embodiments, a set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas the slow axis refers to the axis along which multiple B-scans are collected. The term "cluster scan" may refer to a single unit or block of data generated by repeated acquisitions at the same (or substantially the same) location (or region) to analyze motion contrast, which may identify blood flow. A cluster scan can consist of multiple A-scans or B-scans collected with relatively short time separations at about the same location(s) on the sample. Since the scans in a cluster scan are of the same region, static structures remain relatively unchanged from scan to scan within the cluster scan, whereas motion contrast between the scans that meet predefined criteria may be identified as blood flow.

In various embodiments, B-scans may be created along the horizontal or x-direction, along the vertical or y-direction, along the diagonal of x and y, or in a circular or spiral pattern. B-scans may be in the x-z dimensions but may be any cross-sectional image that includes the z-dimension. An example OCT B-scan image of a normal retina of a human eye is illustrated in FIG. 10. An OCT B-scan of the retina provides a view of the structure of retinal tissue. For illustration purposes, FIG. 10 identifies various canonical retinal layers and layer boundaries. The identified retinal boundary layers include (from top to bottom): the inner limiting membrane (ILM) Lyer1, the retinal nerve fiber layer (RNFL or NFL) Layr2, the ganglion cell layer (GCL) Layr3, the inner plexiform layer (IPL) Layr4, the inner nuclear layer (INL) Layr5, the outer plexiform layer (OPL) Layr6, the outer nuclear layer (ONL) Layr7, the junction between the outer segments (OS) and inner segments (IS) (indicated by reference character Layr8) of the photoreceptors, the external or outer limiting membrane (ELM or OLM) Layr9, the retinal pigment epithelium (RPE) Layr10, and the Bruch's membrane (BM) Layr11.

In OCT Angiography, or Functional OCT, analysis algorithms may be applied to OCT data collected at the same, or about the same, sample locations on a sample at different times (e.g., a cluster scan) to analyze motion or flow (see for example U.S. Patent Publication Nos. 2005/0171438, 2012/0307014, 2010/0027857, 2012/0277579 and U.S. Pat. No. 6,549,801, all of which are herein incorporated in their entirety by reference). An OCT system may use any one of several OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm).

An en face image is a 2D projection of 3D OCT data (e.g., by averaging the intensity of each individual A-scan, such that each A-scan defines a pixel in the 2D projection). Similarly, an en-face vasculature image is an image displaying a motion contrast signal in which the data dimension corresponding to depth (e.g., z-direction along an A-scan) is displayed as a single representative value (e.g., a pixel in a 2D projection image), typically by summing or integrating all or an isolated part of the data (see for example U.S. Pat. No. 7,301,644 herein incorporated in its entirety by reference). OCT systems that provide an angiography imaging functionality may be termed OCT angiography (OCTA) systems.

Figure 11:
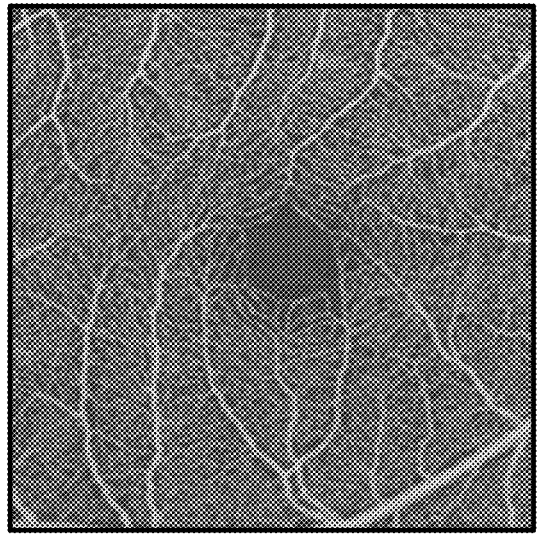
FIG. 11 shows an example image of an en-face vasculature image in accordance with various embodiments.

Referring to FIG. 11, FIG. 11 shows an example of an en-face vasculature image. After processing the data to highlight motion contrast using the motion contrast techniques known in the art, a range of pixels corresponding to a tissue depth from the surface of the internal limiting membrane (ILM) in the retina, may be summed to generate the en face (e.g., frontal view) image of the vasculature.

Figure 12:
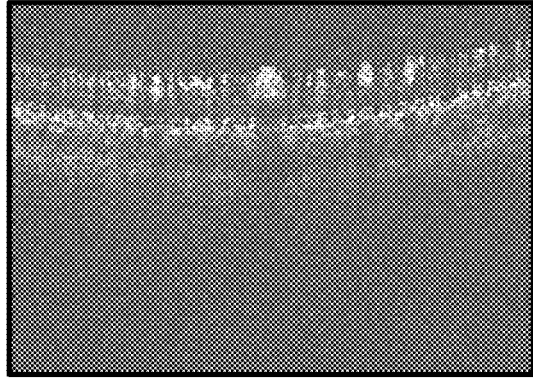
FIG. 12 shows an image of an exemplary B-scan of a vasculature (OCTA) image in accordance with various embodiments.

Referring to FIG. 12, FIG. 12 shows an exemplary B-scan of a vasculature (OCTA) image. As illustrated, structural information may not be well-defined since blood flow may traverse multiple retinal layers making them less defined than in a structural OCT B-scan, as in FIG. 10. Still, OCTA provides a non-invasive technique for imaging the microvasculature of the retina and the choroid, which may be critical to diagnosing and/or tracking various pathologies.

For example, OCTA may identify diabetic retinopathy by identifying microaneurysms, and neovascular complexes, and measuring foveal avascular zone and nonperfused areas. OCTA has been in good agreement with fluorescein angiography (FA), a more traditional, but evasive, technique requiring the injection of a dye to observe vascular flow in the retina. Also, in dry age-related macular degeneration, OCTA has been used to track a general decrease in choriocapillaris flow. Similarly, in wet age-related macular degeneration, OCTA can provide a qualitative and quantitative analysis of choroidal neovascular membranes. OCTA has also been used to study vascular occlusions, e.g., evaluation of non-perfused areas and the integrity of superficial and deep plexus.

Neural Networks

The present invention may use a neural network (NN) machine learning (ML) model. For the sake of completeness, a general discussion of neural networks is provided herein. The present invention may use any, singularly or in combination, of the below-described neural network architecture(s). A neural network, or neural net, is a (nodal) network of interconnected neurons, where each neuron represents a node in the network. Groups of neurons may be arranged in layers, with the outputs of one layer feeding forward to the next layer in a multilayer perceptron (MLP) arrangement. MLP may be understood to be a feedforward neural network model that maps a set of input data onto a set of output data.

Figure 13:
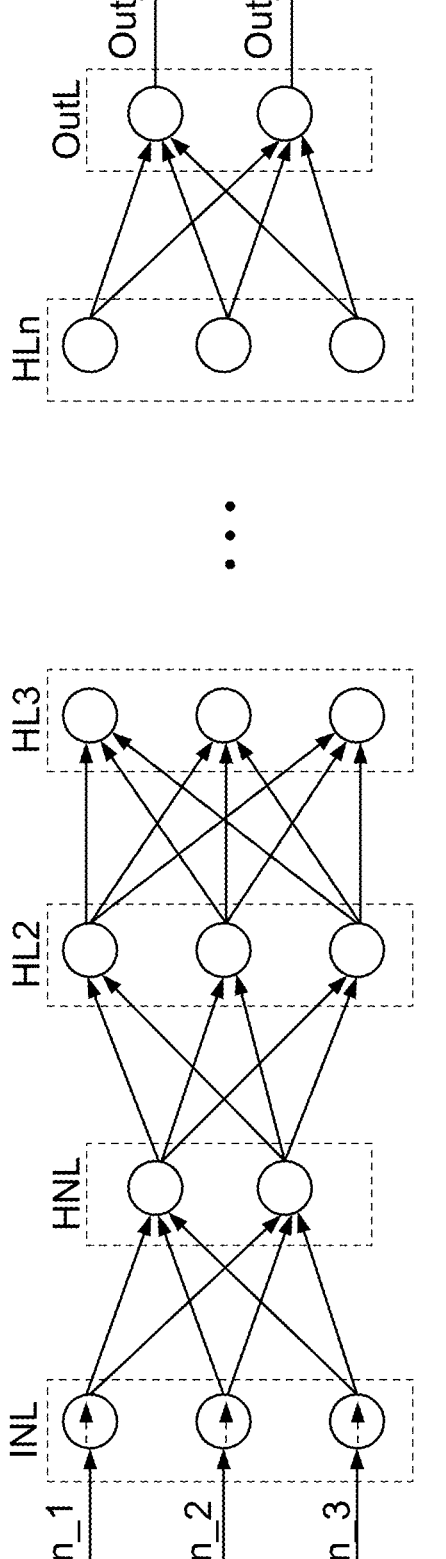
FIG. 13 illustrates a diagram of layers of a set of multiple layers of an example multilayer perceptron (MLP) neural network in accordance with various embodiments.

Referring to FIG. 13, FIG. 13 illustrates an example of a multilayer perceptron (MLP) neural network. Its structure may include multiple hidden (e.g., internal) layers HL1 to HLn that map an input layer InL (that receives a set of inputs (or vector input) in_1 to in_3) to an output layer OutL that produces a set of outputs (or vector output), e.g., out_1 and out_2. Each layer may have any number of nodes, which are herein illustratively shown as circles within each layer. In the present example, the first hidden layer HL1 has two nodes, while hidden layers HL2, HL3, and HLn each have three nodes. Generally, the deeper the MLP (e.g., the greater the number of hidden layers in the MLP), the greater its capacity to learn. The input layer InL receives a vector input (illustratively shown as a three-dimensional vector consisting of in_1, in_2 and in_3), and may apply the received vector input to the first hidden layer HL1 in the sequence of hidden layers. An output layer OutL receives the output from the last hidden layer, e.g., HLn, in the multilayer model, processes its inputs, and produces a vector output result (illustratively shown as a two-dimensional vector consisting of out_1 and out_2).

Typically, each neuron (or node) produces a single output fed forward to neurons in the layer immediately following it. But each neuron in a hidden layer may receive multiple inputs, either from the input layer or from the outputs of neurons in an immediately preceding hidden layer. Each node may apply a function to its inputs to produce an output for that node. Nodes in hidden layers (e.g., learning layers) may apply the same function to their respective input(s) to produce their respective output(s). Some nodes, however, such as the nodes in the input layer InL receive only one input and may be passive, meaning that they simply relay the values of their single input to their output(s), e.g., they provide a copy of their input to their output(s), as illustratively shown by dotted arrows within the nodes of input layer InL.

Figure 14:
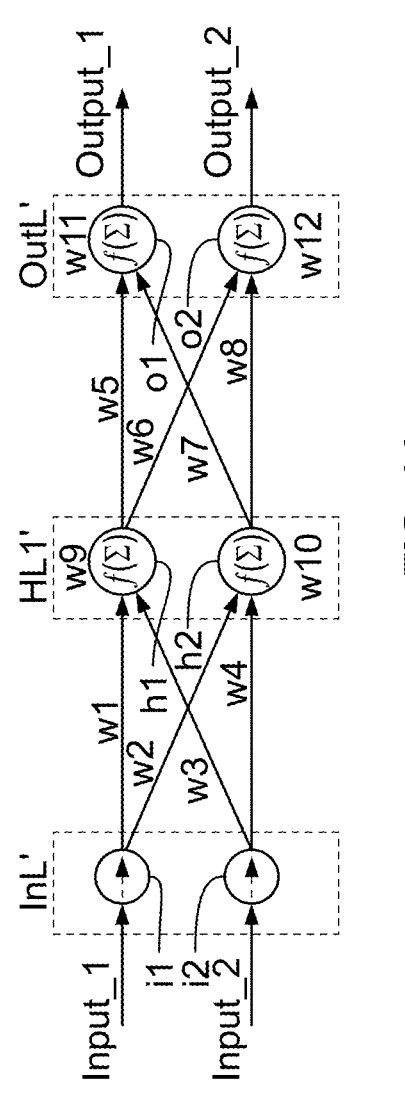
FIG. 14 illustrates a diagram of a neural network consisting of an input layer, a hidden layer, and an output layer in accordance with various embodiments.

For illustration purposes, referring to FIG. 14, FIG. 14 shows a simplified neural network consisting of an input layer InL', a hidden layer HL1', and an output layer OutL'. Input layer InL' is shown as having two input nodes i1 and i2 that respectively receive inputs Input_1 and Input_2 (e.g., the input nodes of layer InL' receive an input vector of two dimensions). The input layer InL' feeds forward to one hidden layer HL1' having two nodes h1 and h2, which feeds forward to an output layer OutL' of two nodes o1 and o2. Interconnections or links, between neurons (illustratively shown as solid arrows), have weights w1 to w8. Typically, except for the input layer, a node (neuron) may receive as input the outputs of nodes in its immediately preceding layer. Each node may calculate its output by multiplying each of its inputs by each input's corresponding interconnection weight, summing the products of its inputs, adding (or multiplying by) a constant defined by another weight or bias that may be associated with that node (e.g., node weights w9, w10, w11, w12 respectively corresponding to nodes h1, h2, o1, and o2), and then applying a non-linear function or logarithmic function to the result. The non-linear function may be termed an activation function or transfer function. Multiple activation functions are known as the art, and the choice of a specific activation function is not critical to the present discussion. It is noted, however, that operation of the ML model, or behavior of the neural net, depends upon weight values, which may be learned so the neural network provides the desired output for a input.

The neural net learns (e.g., is trained to determine) appropriate weight values to achieve the desired output for a input during a training, or learning, stage. Before the neural net is trained, each weight may be individually assigned an initial (e.g., random and optionally non-zero) value, e.g., a random-number seed. Various methods of assigning initial weights are known in the art. The weights are then trained (optimized) so that for a training vector input, the neural network produces an output close to a desired (predetermined) training vector output. For example, the weights may be incrementally adjusted in thousands of iterative cycles by a technique termed back-propagation. In each cycle of back-propagation, a training input (e.g., vector input or training input image/sample) is fed forward through the neural network to determine its actual output (e.g., vector output). An error for each output neuron, or output node, is then calculated based on the actual neuron output and a target training output for that neuron (e.g., a training output image/sample corresponding to the present training input image/sample).

One then propagates back through the neural network (in a direction from the output layer back to the input layer) updating the weights based on how much effect each weight has on the overall error so the output of the neural network moves closer to the desired training output. This cycle is then repeated until the actual output of the neural network is within an acceptable error range of the desired training output for the training input. As it would be understood, each training input may require many back-propagation iterations before achieving a desired error range. Typically, an epoch refers to one back-propagation iteration (e.g., one forward pass and one backward pass) of all the training samples, such that training a neural network may require many epochs. Generally, the larger the training set, the better the performance of the trained ML model, so various data augmentation methods may increase the size of the training set. For example, when the training set includes pairs of corresponding training input images and training output images, the training images may be divided into multiple corresponding image segments (or patches).

Corresponding patches from a training input image and training output image may be paired to define multiple training patch pairs from one input/output image pair, which enlarges the training set. Training on large training sets, however, places high demands on computing resources, e.g. memory and data processing resources. Computing demands may be reduced by dividing a large training set into multiple mini-batches, where the mini-batch size defines the number of training samples in one forward/backward pass. Here, one epoch may include multiple mini-batches. Another issue is the possibility of a NN overfitting a training set such that its capacity to generalize from a specific input to a different input is reduced. Issues of overfitting may be mitigated by creating an ensemble of neural networks or by randomly dropping out nodes within a neural network during training, which effectively removes the dropped nodes from the neural network. Various dropout regulation methods, such as inverse dropout, are known in the art.

It is noted that the operation of a trained NN machine model is not a straightforward algorithm of operational/analyzing steps. When a trained NN machine model receives an input, the input is not analyzed in the traditional sense. Rather, despite the subject or nature of the input (e.g., a vector defining a live image/scan or a vector defining some other entity, such as a demographic description or a record of activity) the input will be subjected to the same predefined architectural construct of the trained neural network (e.g., the same nodal/layer arrangement, trained weight, and bias values, predefined convolution/deconvolution operations, activation functions, pooling operations, etc.), and it may not be clear how the trained network's architectural construct produces its output.

The values of the trained weights and biases are not deterministic and depend upon many factors, such as the time the neural network is given for training (e.g., the number of epochs in training), the random starting values of the weights before training starts, the computer architecture of the machine on which the NN is trained, choice of training samples, distribution of the training samples among multiple mini-batches, choice of the activation function(s), choice of the error function(s) that change the weights, and even if training is interrupted on one machine (e.g., having a first computer architecture) and completed on another machine (e.g., having a different computer architecture). The processing of a neural network on live data cannot be reduced to a simple algorithm of steps. Rather, its operation depends upon its training architecture, training sample sets, training sequence, and various circumstances in the training of the ML model.

In various exemplary embodiments, a NN machine learning model may include a learning (or training) stage and a classification (or operational) stage. In the learning stage, the neural network may be trained for a specific purpose and may be provided with a set of training examples, including training (sample) inputs and training (sample) outputs, and optionally including a set of validation examples to test the progress of the training. During this learning process, various weights associated with nodes and node interconnections in the neural network are incrementally adjusted to reduce an error between the actual output of the neural network and the desired training output. In this manner, a multi-layer feed-forward neural network (such as discussed above) may be made capable of approximating any measurable function to any desired accuracy. The result of the learning stage is a (neural network) machine learning (ML) model learned (e.g., trained). In the operational stage, a set of test inputs (or live inputs) may be submitted to the learned (trained) ML model, which may apply what it has learned to produce an output prediction based on the test inputs.

Like the regular neural networks of FIGS. 13 and 14, convolutional neural networks (CNN) are also made up of neurons that have learnable weights and biases. Each neuron receives inputs, operates (e.g., dot product), and is optionally followed by a nonlinearity. The CNN, however, may receive raw image pixels at one end (e.g., the input end) and provide classification (or class) scores at the other end (e.g., the output end). Because CNN's expect an image as input, they are optimized for working with volumes (e.g., pixel height and width of an image, plus the depth of the image, e.g., color depth such as an RGB depth defined of three colors: red, green, and blue). For example, the layers of a CNN may be optimized for neurons arranged in 3 dimensions. The neurons in a CNN layer may also be connected to a small region of the layer before it, instead of the neurons in a fully-connected NN. The final output layer of a CNN may reduce a full image into a single vector (classification) arranged along the depth dimension.

Figure 15:
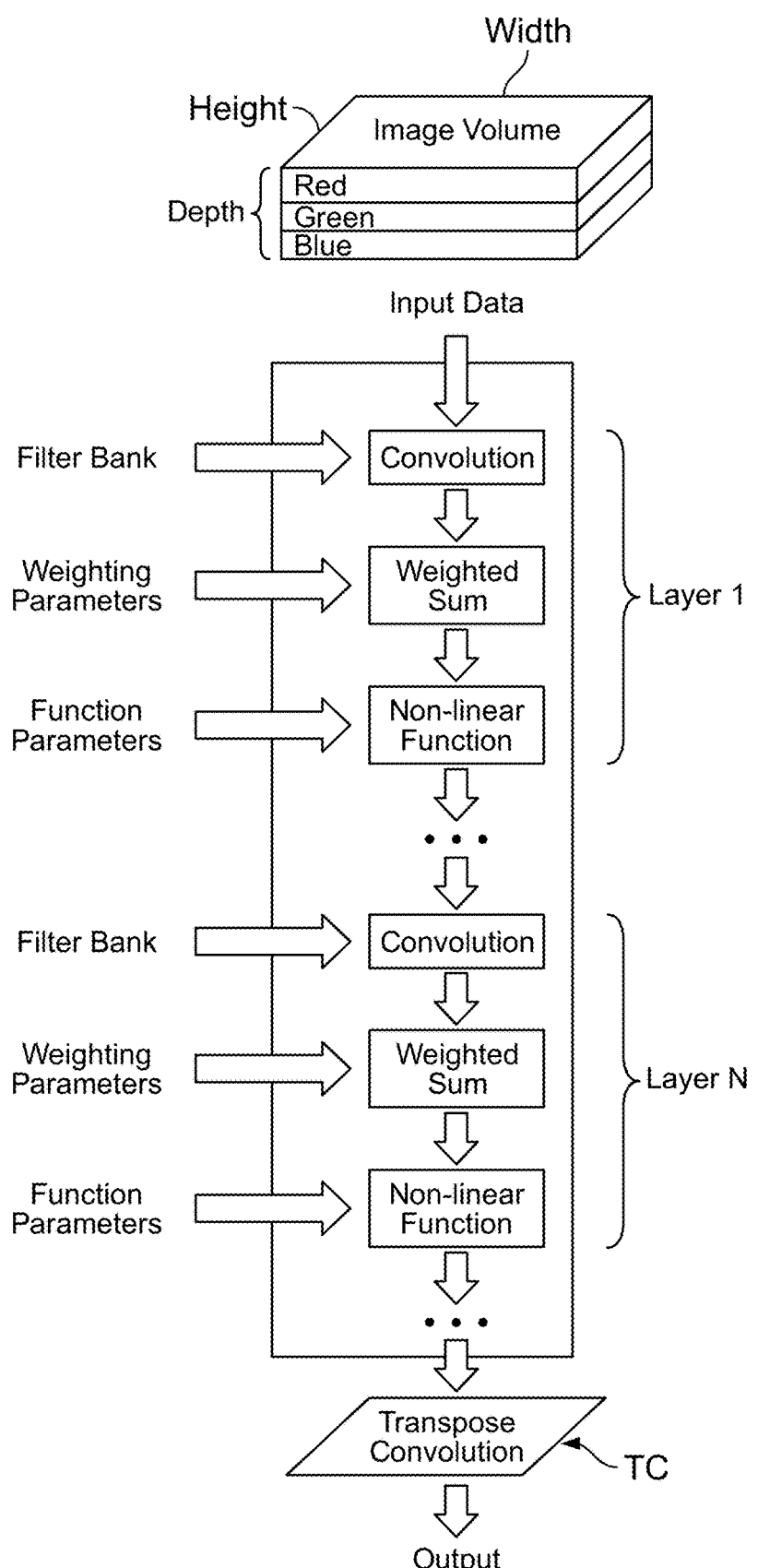
FIG. 15 illustrates a diagram of an example convolutional neural network (CNN) architecture in accordance with various embodiments.

Referring to FIG. 15, FIG. 15 provides an example of convolutional neural network architecture. A convolutional neural network may be defined as a sequence of two or more layers (e.g., Layer 1 to Layer N), where a layer may include an (image) convolution step, a weighted sum (of results) step, and a non-linear function step. The convolution may be performed on its input data by applying a filter (or kernel), e.g., on a moving window across the input data, to produce a feature map. Each layer and part of a layer may have different predetermined filters (from a filter bank), weights (or weighting parameters), and/or function parameters. In the present example, the input data is an image, which may be the raw pixel values of the image, of a pixel height and width. In the present example, the input image is illustrated as having a depth of three-color channels RGB (Red, Green, and Blue). Optionally, the input image may undergo various preprocessing, and the preprocessing results may be input in place of, or in addition to, the raw input image.

Some examples of image preprocessing may include retina blood vessel map segmentation, color space conversion, adaptive histogram equalization, connected parts generation, etc. Within a layer, a dot product may be computed between the weights and a small region they are connected to in the input volume. Many ways of configuring a CNN are known in the art, but as an example, a layer may be configured to apply an elementwise activation function, such as max (0,x) thresholding at zero. A pooling function may be performed (e.g., along the x-y directions) to down sample a volume.

A fully-connected layer may determine the classification output and produce a one-dimensional output vector, which has been found useful for image recognition and classification. However, for image segmentation, the CNN would need to classify each pixel. Since each CNN layer reduces the resolution of the input image, another stage is needed to up-sample the image back to its original resolution. This may be achieved by the application of a transpose convolution (or deconvolution) stage TC, which rarely uses any predefined interpolation method, and instead has learnable parameters.

Convolutional Neural Networks (CNN) can be configured for use to determine computer vision problems in scans. Training a CNN generally requires a large training dataset. The U-Net architecture is based on CNN's and can generally be trained on a smaller training dataset than conventional CNNs.

Figure 16:
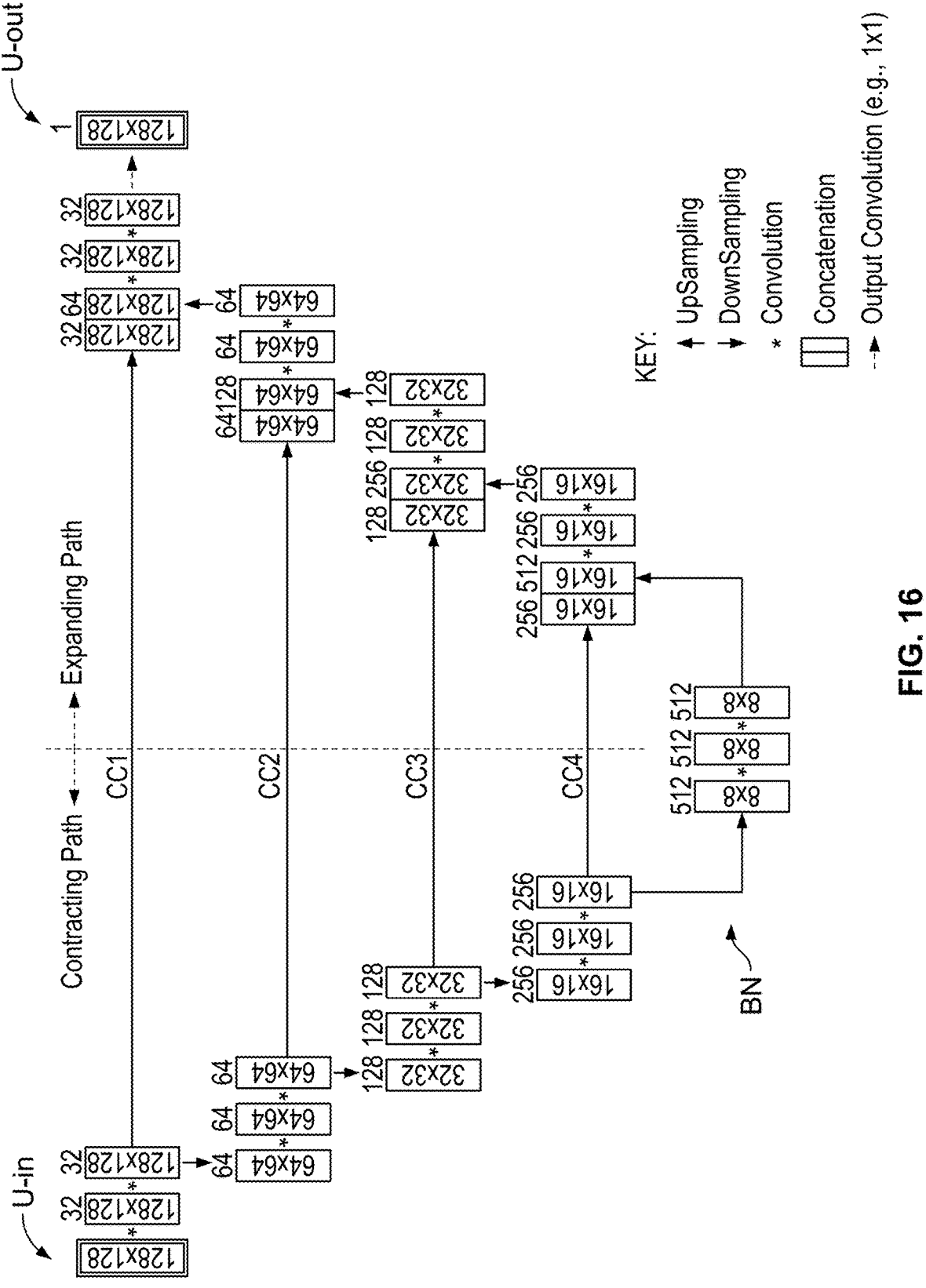
FIG. 16 illustrates a diagram of an example U-Net architecture in accordance with various embodiments.

Referring to FIG. 16, FIG. 16 illustrates an example U-Net architecture. The present exemplary U-Net includes an input module (or input layer or stage) that receives an input U-in (e.g., input image or image patch) of any size. For illustration purposes, the image size at any stage, or layer, is indicated within a box that represents the image, e.g., the input module encloses the number "128×128" to indicate that the input image U-in comprises 128 by 128 pixels. The input image may be a fundus image, an OCT/OCTA en face, a B-scan image, etc. It is to be understood, however, that the input may be of any size or dimension. For example, the input image may be an RGB color image, monochrome image, volume image, etc.

The input image undergoes processing layers, each of which is illustrated with exemplary sizes, but these sizes are for illustration purposes only and would depend, for example, upon the size of the image, convolution filter, and/or pooling stages. The present architecture consists of a contracting path (herein illustratively comprised of four encoding modules) followed by an expanding path (herein illustratively comprised of four decoding modules), and copy-and-crop links (e.g., CC1 to CC4) between corresponding modules/stages that copy the output of one encoding module in the contracting path and concatenates it to (e.g., appends it to the back of) the up-converted input of a correspond decoding module in the expanding path. This results in a typical U-shape, from which the architecture draws its name. Optionally, such as for computational considerations, a "bottleneck" module/stage (BN) may be positioned between the contracting path and the expanding path. The bottleneck BN may consist of two convolutional layers (with batch normalization and optional dropout).

The contracting path is like an encoder, and generally captures context (or feature) information by feature maps. In the present example, each encoding module in the contracting path may include two or more convolutional layers, illustratively indicated by an asterisk symbol "*", and which may be followed by a max pooling layer (e.g., DownSampling layer). For example, input image U-in is illustratively shown to undergo two convolution layers, each with 32 feature maps. As it would be understood, each convolution kernel produces a feature map (e.g., the output from a convolution operation with a kernel is an image typically termed a "feature map"). For example, input U-in undergoes a first convolution that applies 32 convolution kernels (not shown) to produce an output consisting of 32 respective feature maps. However, as it is known in the art, the number of feature maps produced by a convolution operation may be adjusted (up or down). For example, the number of feature maps may be reduced by averaging groups of feature maps, dropping some feature maps, or other known methods of feature map reduction. In the present example, this first convolution is followed by a second convolution whose output is limited to 32 feature maps. Another way to envision feature maps may be to think of the output of a convolution layer as a 3D image whose 2D dimension is given by the listed X-Y planar pixel dimension (e.g., 128×

128 pixels), and whose depth is given by the number of feature maps (e.g., 32 planar images deep). Following this analogy, the output of the second convolution (e.g., the output of the first encoding module in the contracting path) may be described as a 128×128×32 image. The output from the second convolution then undergoes a pooling operation, which reduces the 2D dimension of each feature map (e.g., the X and Y dimensions may each be reduced by half).

The pooling operation may be embodied within the Down Sampling operation, as indicated by a downward arrow. Several pooling methods, such as max pooling, are known in the art and the specific pooling method is not critical to the present invention. The number of feature maps may double at each pooling, starting with 32 feature maps in the first encoding module (or block), 64 in the second encoding module, and so on. The contracting path thus forms a convolutional network consisting of multiple encoding modules (or stages or blocks). As is typical of convolutional networks, each encoding module may provide at least one convolution stage followed by an activation function (e.g., a rectified linear unit (ReLU) or sigmoid layer), not shown, and a max pooling operation. Generally, an activation function introduces nonlinearity into a layer (e.g., to help avoid overfitting issues), receives the results of a layer, and determines whether to "activate" the output (e.g., determines whether the value of a node meets predefined criteria to have an output forwarded to a next layer/node). The contracting path generally reduces spatial information while increasing feature information.

The expanding path is like a decoder, and may provide localization and spatial information for the results of the contracting path, despite the down sampling and any max-pooling performed in the contracting stage. The expanding path includes multiple decoding modules, where each decoding module concatenates its current up-converted input with the output of a corresponding encoding module. In this manner, feature and spatial information are combined in the expanding path through a sequence of up-convolutions (e.g., Up Sampling or transpose convolutions or deconvolutions) and concatenations with high-resolution features from the contracting path (e.g., via CC1 to CC4). Thus, the output of a deconvolution layer is concatenated with the corresponding (optionally cropped) feature map from the contracting path, followed by two convolutional layers and an activation function (with optional batch normalization).

The output from the last expanding module in the expanding path may be fed to another processing/training block or layer, such as a classifier block, that may be trained along with the U-Net architecture. Or in addition, the output of the last up sampling block (at the end of the expanding path) may be submitted to another convolution (e.g., an output convolution) operation, as indicated by a dotted arrow, before producing its output U-out. The kernel size of output convolution may be selected to reduce the dimensions of the last up sampling block to the desired size. For example, the neural network may have multiple features per pixel right before reaching the output convolution, which may provide a 1×1 convolution operation to combine these multiple features into a single output value per pixel, on a pixel-by-pixel level.

Computing Device/System.

Referring to FIG. 17, FIG. 17 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud parts in one or more networks.

In some embodiments, the computer system may include a processor Cpnt1, memory Cpnt2, storage Cpnt3, an input/output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on the graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, and one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers and may include one or more arithmetic logic units (ALUs). Processor Cpnt1 may be a multi-core processor or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal registers or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2, or storage Cpnt3. Bus Cpnt6 may include one or more memory buses (which may each include an address bus and a data bus) and may couple processor Cpnt1 to memory Cpnt2 and/or storage Cpnt3.

Optionally, one or more memory management units (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, a magneto-optical disc, magnetic tape, Universal Serial Bus (USB)-accessible drive, or other types of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these features.

Communication interface Cpnt5 may provide network interfaces for communication with other systems or networks. Communication interface Cpnt5 may include a Bluetooth interface or other types of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as a Global System for Mobile Communications (GSM) network), the Internet, or a combination of two or more of these.

Bus Cpnt6 may provide a communication link between the above-mentioned parts of the computing system. For example, bus Cpnt6 may include an Accelerated Graphics Port (AGP) or other graphics bus, an Enhanced Industry Standard Architecture (EISA) bus, a front-side bus (FSB), a Hyper Transport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these features.

Herein, a computer-readable non-transitory storage medium or media may include one or more semiconductor-based or other integrated circuits (ICs) (such, as field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Figure 18:
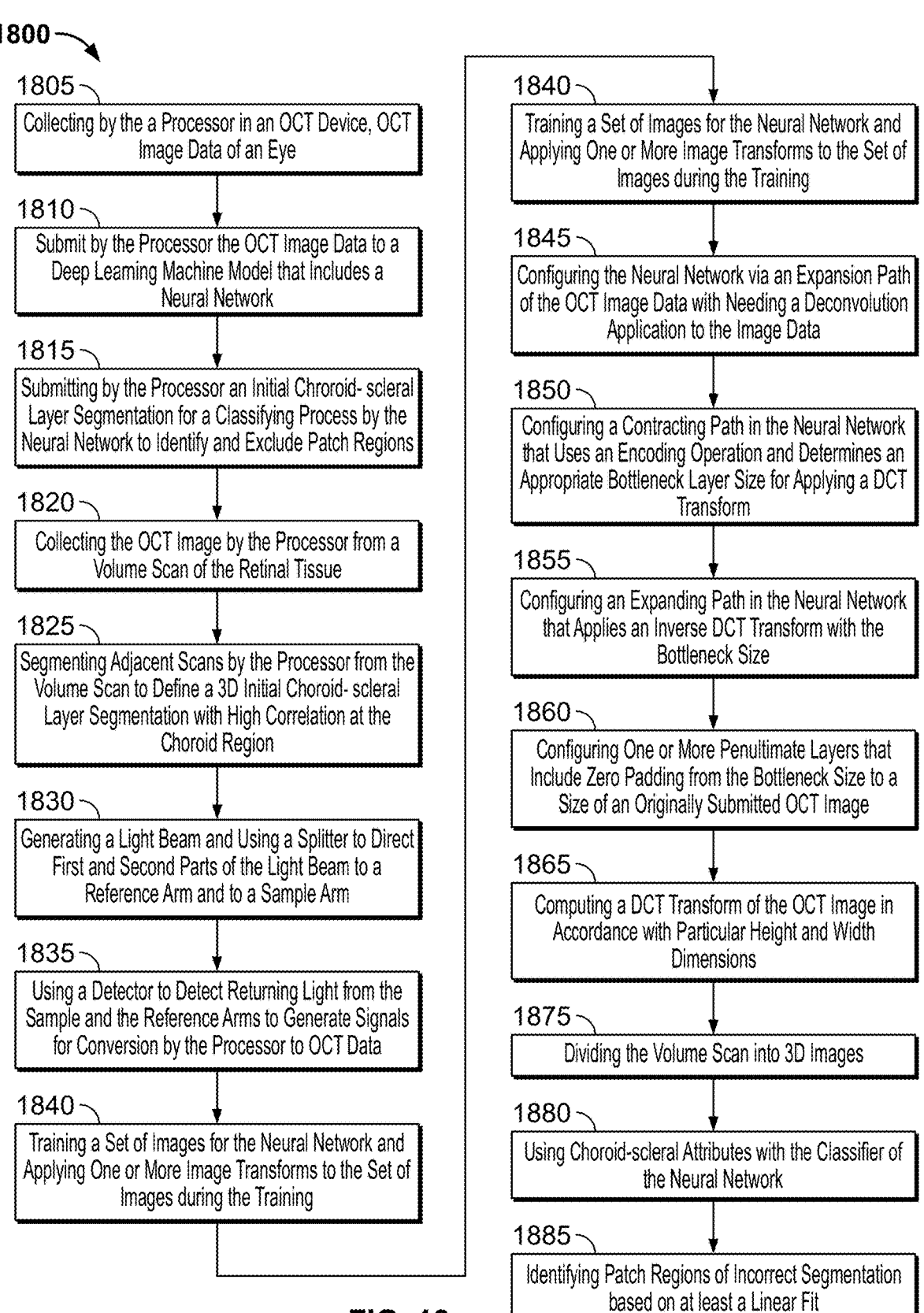
FIG. 18 illustrates an exemplary flowchart of the process of the classifying by the neural network of the choroid-scleral layer segmentation in accordance with various embodiments.

Referring to FIG. 18, FIG. 18 illustrates an exemplary flowchart 1800 of the process of the classifying (classification module) by the neural network of the choroid-scleral layer segmentation in accordance with various embodiments.

At step 1805, a method for segmenting a choroid-scleral layer from optical coherence tomography (OCT) image data of an eye is initiated by collecting by a processor configured with an OCT device, OCT image data of the eye. At step 1810, the OCT image data is received by the processor for submission to a deep learning machine model based on a neural network that produces an initial choroid-scleral layer segmentation. In various embodiments, the neural network is configured with a contracting path including a plurality of convolution layers followed by a maximum pooling layer; and an expanding path following the contracting path, the expanding path including at least one discrete cosine transform (DCT) decoder. At step 1815, the OCT image data that comprises the initial choroid-scleral layer segmentation is submitted by the processor to a classification module/process by the neural network to identify and exclude, from the initial choroid-scleral layer segmentation, patch regions considered to have incorrect segmentation and define a final choroid-scleral layer segmentation. At step 1820, the collected OCT image data is configured from a volume scan, and the deep learning machine model requires the submission of a plurality of adjacent B-scans from the volume scan to produce the initial choroid-scleral layer segmentation. At step 1825, the plurality of adjacent B-scans from the volume scan are segmented simultaneously to define an 3D initial choroid-scleral layer segmentation with high correlation at the choroid region, and the deep learning model enforces continuity of the segmented initial choroid-scleral layer between the plurality of adjacent B-scans. At step 1830, the OCT device generates a beam of light from a light source and uses a beam splitter having a beam-splitting surface for directing a first part of the light into a reference arm and a second part of the light into a sample arm. Also, optics in the OCT device are used for directing the light in the sample arm to one or more locations on a sample. At step 1835, a detector is implemented for receiving light returning from the sample and reference arms and generating signals in response to the receipt of the light, the processor is configured to convert signals associated with the receipt of the light to OCT image data. At step 1840, the deep learning machine model applied by the processor, implements a neural network trained (i.e., a supervised training) by a set of training input images and a set of training output images, where each training output image is based on a corresponding training input image that has undergone attenuation correction, including removing of vessel shadows and improving contrast.

At step 1850, the expanding path is configured in the neural network without (i.e., lacking) any deconvolution process applied to the OCT image data. Also, the contracting path includes a relu-nonlinearity with 3×3 filter size followed by the maximum pooling layer.

At step 1860, the contracting path is configured to define an encoding operation, and the maximum pooling layer used in the neural network determines a bottleneck size of an encoder operation that reflects a preferred energy distribution of the discrete cosine transform using in the decoding process. At step 1865, the expanding path is configured to define a decoding process, and the first step in the decoding process of a decoder is an inverse cosine transform with the bottleneck size and followed by a plurality of convolutional layers.

At step 1865, one or more penultimate layers of the decoder are configured to include zero-padding from the bottleneck size to a size of an originally submitted OCT image data combined with the discrete cosine transform to enable application of an image up-sampling function. At step 1870, the processor computes using at least one discrete cosine transform (DCT) decoder, the discrete cosine transform along the width and height dimensions. At step 1875, the volume scan by the OCT device is divided by the processor into 3D patches where each patch includes the OCT image data of an eye from the volume scan, and the OCT image data is submitted to the deep learning machine model via a single one of the 3D patches. At step 1880, the classifier of the neural network uses choroid-scleral interface attributes, including an attribute of smooth surface with low frequency part, to identify incorrect segmentation patch regions of the initial choroid-scleral layer. Also identified by the processor at step 1885, are patch regions of incorrect segmentation based on a linear fit between the choroid-scleral interface and a smooth surface; and patch regions of incorrect segmentation based on one or more of outlier patches from a maximum curvature or arclength, unrealistic shapes defined as deviating beyond a predefined amount from a library of acceptable shapes, and choroid-scleral interface modeling based on polynomial, Zernike, or Gridfit.

Although this disclosure describes and illustrates a particular computer system having a particular number of particular parts in a particular arrangement, this disclosure contemplates any suitable computer system having any suitable number of any suitable parts in any suitable arrangement.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications, and variations as may fall within the spirit and scope of the appended claims.

What is claimed:

1. A method for segmenting a choroid-scleral layer from optical coherence tomography (OCT) image data of an eye, comprising:

collecting the OCT image data of the eye from an OCT system;

submitting the OCT image data to a deep learning machine model based on a neural network, and producing an initial choroid-scleral layer segmentation, the neural network having:

a contracting path including a plurality of convolution layers followed by a max pooling layer; and an expanding path following the contracting path, the expanding path including at least one discrete cosine transform (DCT) decoder; and submitting the initial choroid-scleral layer segmentation to a classification module to identify and exclude, from the initial choroid-scleral layer segmentation, patch regions deemed to have incorrect segmentation and define a final choroid-scleral layer segmentation.

2. The method of claim 1, wherein the collected OCT image data is a volume scan, and the deep learning machine model uses a submission of a plurality of adjacent B-scans from the volume scan to produce the initial choroid-scleral layer segmentation.

3. The method of claim 2, wherein the plurality of adjacent B-scans from the volume scan are segmented simultaneously to define an 3D initial choroid-scleral layer segmentation with high correlation at a choroid region, and a deep learning model that enforces continuity of the segmented initial choroid-scleral layer between the plurality of adjacent B-scans.

4. The method of claim 1, wherein the collected OCT image data is a volume scan collected using an OCT system including:

a light source for generating a beam of light;

a beam splitter having a beam-splitting surface for directing a first portion of the light into a reference arm and a second portion of the light into a sample arm;

optics for directing the light in the sample arm to one or more locations on a sample;

a detector for receiving light returning from the sample and reference arms and generating signals in response thereto; and a processor for converting the signals into OCT image data.

5. The method of claim 1, wherein the deep learning machine model is based on a neural network trained using a set of training input images and a set of training output images, and wherein each training output image is based on a corresponding training input image that has undergone attenuation correction, including removing of vessel shadows and improving contrast.

6. The method of claim 1, wherein the expanding path lacks any deconvolution module.

7. The method of claim 1, wherein the contracting path includes a relu-nonlinearity with 3×3 filter size followed by the max pooling layer.

8. The method of claim 1, wherein the contracting path defines an encoder, and wherein the max pooling layer determines a bottleneck size of the encoder that best reflects energy distribution of a discrete cosine transform decoder.

9. The method of claim 8, wherein the expanding path defines a decoder, and wherein a first step in a decoding operation of the decoder is an inverse cosine transform with the bottleneck size and followed by the plurality of convolutional layers.

10. The method of claim 9, wherein penultimate layers of the decoder includes zero-padding from the bottleneck size to the size of the originally submitted OCT image data combined with the discrete cosine transform to provide an image up-sampling function.

11. The method of claim 1, wherein the at least one discrete cosine transform (DCT) decoder computes the discrete cosine transform along the width and height dimensions.

12. The method of claim 1, wherein the OCT image data of an eye is a volume scan, wherein the volume scan is divided into 3D patches, and wherein the OCT image data submitted to the deep learning machine model is a 3D patch.

13. The method of claim 1, wherein the classification module uses choroid-scleral interface attributes, including an attribute of smooth surface with low frequency component, to identify incorrect segmentation patch regions of the initial choroid-scleral layer.

14. The method of claim 1, wherein the classification module identifies patch regions of incorrect segmentation based on a linear fit between a choroid-scleral interface and a smooth surface.

15. The method of claim 14, wherein the classification module identifies patch regions of incorrect segmentation based on one or more of outlier patches from a max curvature or arclength, unrealistic shapes defined as deviating beyond a predefined amount from a library of acceptable shapes, and choroid-scleral interface modeling based on polynomial, Zernike, or Gridfit.

16. D) A system for segmenting a choroid-scleral layer from an optical coherence tomography (OCT) volume scan image data of an eye, comprising:

a light source for generating a beam of light;

optics for directing the light to one or more locations on a sample including the eye;

a detector for receiving light returning from the sample and generating signals in response thereto; and a processor operably coupled to the detector and configured to:

define the volume scan image data from the generated signals, submit the volume scan image data to a deep learning machine model based on a neural network, and producing an initial choroid-scleral layer segmentation, wherein the neural network comprises:

a contracting path including a plurality of convolution layers followed by a max pooling layer; and an expanding path following the contracting path, the expanding path including at least one discrete cosine transform (DCT) decoder; and submitting the initial choroid-scleral layer segmentation to a classification module to identify and exclude, from the initial choroid-scleral layer segmentation, patch regions deemed to have incorrect segmentation and define a final choroid-scleral layer segmentation.

17. The system of claim 16, wherein a plurality of adjacent B-scans from the volume scan image data are segmented simultaneously to define an 3D initial choroid-scleral layer segmentation with high correlation at a choroid region, and a deep learning model that enforces continuity of the segmented initial choroid-scleral layer between the plurality of adjacent B-scans.

18. The system of claim 16, wherein the expanding path lacks any deconvolution module.

19. The system of claim 16, wherein the contracting path defines an encoder, and the max pooling layer determines a bottleneck size of the encoder that best reflects the energy distribution of the discrete cosine transform decoder.

20. The system of claim 19, wherein the expanding path defines a decoder, and a first step in a decoding operation of the decoder is an inverse cosine transform with the bottleneck size and followed by a plurality of convolutional layers.

* * * * *